(12) United States Patent
Wilson et al.

(10) Patent No.: US 10,287,108 B2
(45) Date of Patent: *May 14, 2019

(54) SYSTEMS AND APPARATUS WITH FALLEN CONTAINER DETECTION

(71) Applicant: bioMerieux, Inc., Durham, NC (US)

(72) Inventors: Mark S. Wilson, Hillsborough, NC (US); James Knebel, Edwardsville, IL (US); Thierry Vivet, Maryland Heights, MO (US)

(73) Assignee: bioMérieux, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/012,824

(22) Filed: Jun. 20, 2018

(65) Prior Publication Data

US 2018/0297791 A1     Oct. 18, 2018

Related U.S. Application Data

(60) Continuation of application No. 15/265,892, filed on Sep. 15, 2016, now Pat. No. 10,023,398, which is a
(Continued)

(51) Int. Cl.
*B65G 47/84* (2006.01)
*G01N 35/00* (2006.01)
(Continued)

(52) U.S. Cl.
CPC .......... *B65G 47/846* (2013.01); *B65G 43/08* (2013.01); *C12M 41/36* (2013.01); *G01B 11/14* (2013.01); *G01N 35/00603* (2013.01); *G01N 35/00623* (2013.01); *G01N 35/04* (2013.01); *B65G 2201/0235* (2013.01);
(Continued)

(58) Field of Classification Search
CPC ............... B65G 47/864; B65G 47/846; G01N 2035/00643
See application file for complete search history.

(56) References Cited

U.S. PATENT DOCUMENTS 3,827,812 A * 8/1974 Heimann .............. B07C 5/3404
209/524
4,277,928 A * 7/1981 Ahlers ..................... B67B 3/06
53/67
(Continued)

FOREIGN PATENT DOCUMENTS

DE     10007627     9/2001
JP     S4820391     6/1973

*Primary Examiner* — Thomas Randazzo
(74) *Attorney, Agent, or Firm* — Myers Bigel, P.A.

(57) ABSTRACT

Systems and apparatus with circuits that are configured to detect fallen containers upstream or proximate an intake zone suitable for automated evaluation apparatus using different sensors, including at least one lower sensor and at least one upper sensor which is positioned to project an optical signal at a height corresponding to a top portion of an upright container to thereby allow an increased reliability in detection of different orientations and positions of fallen containers. An optional second lower sensor may be used which is longitudinally spaced apart from the first lower sensor and the lower sensors can transmit optical signals across the container travel path that do not intersect.

30 Claims, 17 Drawing Sheets

Related U.S. Application Data division of application No. 13/796,874, filed on Mar. 12, 2013, now Pat. No. 9,470,510.

(60) Provisional application No. 61/617,210, filed on Mar. 29, 2012.

(51) Int. Cl.
  *G01B 11/14* (2006.01)
  *B65G 43/08* (2006.01)
  *G01N 35/04* (2006.01)
  *C12M 1/34* (2006.01)

(52) U.S. Cl.
  CPC .............. *B65G 2203/044* (2013.01); *G01N 2035/00643* (2013.01); *G01N 2035/0465* (2013.01)

(56) References Cited

U.S. PATENT DOCUMENTS

| | | | |
|---|---|---|---|
| 4,421,542 A * | 12/1983 | Poad | B07C 5/122 209/3.2 |
| 4,494,656 A * | 1/1985 | Shay | G01V 8/12 209/524 |
| 4,945,060 A | 7/1990 | Turner et al. | |
| 5,094,955 A | 3/1992 | Calandra et al. | |
| 5,162,229 A | 11/1992 | Thorpe et al. | |
| 5,164,796 A | 11/1992 | Di Guiseppi et al. | |
| 5,217,876 A | 6/1993 | Turner et al. | |
| 5,679,206 A | 10/1997 | Glass | |
| 5,795,773 A | 8/1998 | Read et al. | |
| 5,810,955 A * | 9/1998 | Seifert | B65C 9/067 156/362 |
| 5,817,507 A | 10/1998 | Berndt | |
| 5,856,175 A | 1/1999 | Thorpe et al. | |
| 6,177,050 B1 | 1/2001 | Bybee et al. | |
| 6,293,750 B1 | 9/2001 | Cohen et al. | |
| 6,365,906 B1 * | 4/2002 | Spangenberg | B65G 47/256 250/223 B |
| 6,769,228 B1 * | 8/2004 | Mahar | B65B 61/20 53/155 |
| 6,961,638 B2 * | 11/2005 | Ouellette | B07C 5/3408 198/395 |
| 7,684,034 B2 * | 3/2010 | Sones | G01N 21/9036 356/240.1 |
| 8,142,740 B2 * | 3/2012 | Self | B01L 9/06 206/139 |
| 8,333,053 B2 * | 12/2012 | Mahar | G01G 19/4148 53/238 |
| 8,694,151 B2 * | 4/2014 | Jendrichowski | B65G 47/912 198/395 |
| 9,470,510 B2 * | 10/2016 | Wilson | G01B 11/14 |
| 2003/0040104 A1 | 2/2003 | Barbera-Guillem | |
| 2005/0220670 A1 | 10/2005 | Palmieri et al. | |
| 2006/0216199 A1 | 9/2006 | Koike | |
| 2009/0279082 A1 * | 11/2009 | Till | B07C 5/3408 356/240.1 |
| 2010/0068755 A1 | 3/2010 | Walsh et al. | |
| 2011/0124028 A1 | 5/2011 | Robinson et al. | |
| 2011/0125314 A1 * | 5/2011 | Robinson | C12Q 1/04 700/228 |
| 2013/0126042 A1 * | 5/2013 | Dewald | G07F 11/44 141/105 |
| 2017/0241875 A1 * | 8/2017 | McKeen | G01N 1/312 |

\* cited by examiner

| CONDITION | | SENSOR CONFIGURATION | | |
|---|---|---|---|---|
| | | 1 | 2 | 3 |
| 4. | - FALLEN BOTTLE<br>- LES FIRST<br>- INDEXER POCKET 1<br>- PARTIALLY ENGAGED IN POCKET | X | X | |

FIG. 11D

| CONDITION | | SENSOR CONFIGURATION | | |
|---|---|---|---|---|
| | | 1 | 2 | 3 |
| 5. | - FALLEN BOTTLE<br>- BRIDGE BLOCKED<br>- CAP ORIENTED TO FRONT | | X | |

| CONDITION | | SENSOR CONFIGURATION | | |
|---|---|---|---|---|
| | | 1 | 2 | 3 |
| 6. • FALLEN BOTTLE<br>• INDEXER BLOCKED<br>• CAP ORIENTED TO REAR | | | X | |

FIG. 11G

| CONDITION | | SENSOR CONFIGURATION | | |
|---|---|---|---|---|
| | | 1 | 2 | 3 |
| 7. • FALLEN BOTTLE<br>• INDEXER BLOCKED<br>• CAP ORIENTED TO REAR<br>• LES ROTATED CLOCKWISE | | | X | |

FIG. 11J

| CONDITION | | SENSOR CONFIGURATION | | |
|---|---|---|---|---|
| | | 1 | 2 | 3 |
| 10. | • FALLEN BOTTLE<br>• INDEXER BLOCKED<br>• CAP ORIENTED TO REAR<br>• STANDING BOTTLES BLOCKED | X | X | |

FIG. 11K

| CONDITION | | SENSOR CONFIGURATION | | |
|---|---|---|---|---|
| | | 1 | 2 | 3 |
| 11. | • FALLEN BOTTLE<br>• INDEXER BLOCKED<br>• CAP ORIENTED TO REAR<br>• STANDING BOTTLES BLOCKED | X | X | |

SYSTEMS AND APPARATUS WITH FALLEN CONTAINER DETECTION

RELATED APPLICATIONS

This application is a continuation of U.S. patent application Ser. No. 15/265,892, filed Sep. 15, 2016, which is a divisional application of U.S. patent application Ser. No. 13/796,874, filed Mar. 12, 2013, now U.S. Pat. No. 9,470,510, issued Oct. 18, 2016, which claims priority to and the benefit of U.S. Provisional Application Ser. No. 61/617,210, filed Mar. 29, 2012, the contents of which are hereby incorporated by reference as if recited in full herein.

BACKGROUND

Conveyor systems that merge into a wheel for serially loading containers, such as bottles or tubes, so that the groups or queues of containers can be presented individually for processing can be desirable for automated systems such as those described in Automated Microbial Detection Apparatus, such as described in U.S. 2011/0124028, the content of which is hereby incorporated by reference as if recited in full herein. The height to width ratio of elongated containers such as bottles or tubes can be problematic, particularly when they are provided as mostly unsupported upright containers on a moving floor such as a conveyor. Fallen bottles, if not detected, can jam or cause misfeed errors that can decrease operational speed and/or damage components of the system. One method used to detect fallen bottles employs vertically stacked pairs of front and back sensors to attempt to identify whether test sample containers have fallen. The upper sensor is located at a position that is higher than a diameter of the bottle while the lower sensor is positioned no higher than the diameter of the bottle. If a bottle tips or falls over, the lower sensor is triggered while the upper one is not. This "fault condition" can be used to generate an operator alert. However, where there are queues of more than one container deep and one has fallen over with another upright container behind it, the upper sensor may detect the upright bottle, so the stacked pair of sensors then fails to detect the fault. Also, the reflective nature of transparent or translucent materials such as glass or polymer containers (e.g., plastic) can have labels applied to the container, varying fluid content, orientations and the like that can that can alter detection reliability.

SUMMARY

Embodiments of the invention provide a reliable optical detection system for fallen elongated containers that can have different fall or jam positions.

Embodiments of the invention are directed to methods, systems, computer program products, apparatus and circuits configured to detect fallen containers upstream and/or inside a pocket of a rotating (index) wheel using at least two different sensors, at least one lower sensor that is positioned proximate an intake zone and/or loading position configured to project an optical signal across a container travel path, and at least one upper sensor which is positioned to project an optical signal at a height that is above the optical signal of the at least one lower sensor, the upper sensor optical signal height corresponding to a top portion of an upright container to thereby allow an increased reliability in detection of different orientations and positions of fallen containers.

Some embodiments are directed to automated misfeed and/or fallen container detection systems that include a conveyor providing a travel path for groups of two or more elongated containers, a rotating wheel in cooperating alignment with the conveyor, the wheel having a plurality of circumferentially spaced apart pockets, each pocket configured to accept a single upright elongated container, and a plurality of spaced apart sensors. The sensors include at least one lower sensor configured to transmit a respective optical signal across the container travel path proximate the wheel at a height that is less than a width of the containers. The at least one lower sensor including a first lower sensor that transmits a respective first optical signal across a front edge portion of a pocket of the wheel facing the conveyor at a loading position. The sensors also include at least one upper sensor that is positioned proximate the wheel configured to transmit an optical signal at a height corresponding to a top portion of an upright container to thereby allow detection of different orientations and positions of fallen containers and/or container jam or blockage conditions.

The at least one lower sensor can include a first lower sensor and a second lower sensor, with the second lower sensor positioned longitudinally spaced apart from the first lower sensor. In some embodiments, the first lower sensor can reside downstream from the second lower sensor. Each of the first and second lower sensors can reside proximate the rotating wheel. The first and second lower sensors can be configured to transmit respective first and second non-intersecting first and second optical signals at a height that is below a width dimension of the containers across the conveyor container travel path proximate the rotating wheel. In some embodiments, the first and second lower sensors can transmit non-intersecting respective first and second optical signals at a height that is no greater than a diameter of the elongated container having a round cross-section and/or base.

The system can include a plurality of containers on the conveyor. The containers can be optically transmissive tubes with a top cap with one size with an outer diameter. The first sensor can be positioned to transmit a respective optical signal at a height that is no greater than the diameter of the containers.

The first and second lower sensors can have optical signals that diverge away from each other as they project across the conveyor so that the first and second optical signals are closer together on one side of the conveyor travel path relative to an opposing side of the travel path.

The system can include a control circuit that is configured to direct the wheel to rotate a defined distance then stop to receive a container from a container queue on the conveyor. The control circuit can be configured to rotate the wheel when data from the third sensor confirms an upright container is in position in a receiving pocket of the wheel.

The system can include a control circuit that is configured to direct the conveyor to reverse direction when a fault condition is identified based on data from at least one of the at least one lower and upper sensors.

The system can be configured to direct the wheel to rotate with an empty receiving pocket to an indexed position when a fault condition associated with a fallen container is identified as located away from the receiving pocket based on data from the at least one lower sensor and the at least one upper sensor.

The travel path can narrow in width as it approaches the wheel. The system can further include a curved sidewall that is concave proximate an outer perimeter of the wheel. The at least one lower sensor can be a retroreflective sensor that transmits the first optical signal through a front edge portion of the receiving pocket.

The second lower sensor can be a retroreflective sensor. The second optical signal can cross the conveyor travel path a distance "D" away from the first optical signal. In particular embodiments, the distance D is greater than one diameter but less than two diameters of the elongated containers transported by the conveyor.

The travel path can narrow in width as it approaches the wheel to a width that is less than four container diameters. The system can include a control circuit that is configured to identify a "bridge" of frictionally engaged upright containers based on data from at least the second lower sensor, then automatically reverse direction of the conveyor to dislodge the bridge.

The system can include a plurality of containers on the conveyor. The containers can be optically transmissive tubes with a top cap holding biospecimens. The first lower sensor can be positioned to transmit the first optical signal at a height that is no greater than an outer diameter of the containers.

At least some of the containers may include blood samples.

The system can also include a control circuit that is configured to monitor the at least one upper sensor for a short interval after a fallen container fault is identified based on data from the at least one lower sensor to assess whether a container enters a receiving pocket of the wheel before generating a fallen container notification.

Still other embodiments are directed to an automated detection apparatus for detection of microorganism growth in test samples. The apparatus includes: (a) a housing enclosing an interior temperature controlled chamber; (b) a container loading system comprising a conveyor defining a travel path that transports groups of elongated containers with test samples to the housing for processing; (c) a rotating wheel in cooperating alignment with the conveyor, the wheel having a plurality of circumferentially spaced apart pockets, each pocket configured to accept a single elongated container; (d) a detection device located within the housing configured to detect microorganism growth in specimen containers loaded into the housing; and (e) a plurality of spaced apart sensors residing proximate the wheel. The sensors can include at least one lower sensor including at least a first lower sensor configured to transmit a respective optical signal across a portion of the wheel at a loading position and at least one upper sensor. The at least one upper sensor can be positioned to transmit a respective upper optical signal at a height that is above the at least one lower sensor optical signal. The height corresponds to a top portion of an upright container to thereby allow detection of different orientations and positions of containers.

The at least one lower sensor can include the first lower sensor and a second lower sensor with the lower sensors positioned longitudinally spaced apart from each other. The first lower sensor can be farther downstream than the second lower sensor. The first and second lower sensors can be configured to transmit respective first and second non-intersecting first and second optical signals across the conveyor container travel path proximate the rotating wheel, and wherein a height of each of the first and second optical signals is below a width dimension of the containers.

The apparatus can include a plurality of containers on the conveyor. The containers can be optically transmissive tubes with a top cap and have a common size with an outer diameter. The at least one lower sensor can be positioned to transmit respective optical signals at a height that is no greater than the diameter of the containers.

The first and second optical signals can diverge away from each other as the signals project across the conveyor so that the first and second optical signals are closer together on one side of the conveyor travel path relative to an opposing side of the travel path.

The apparatus can include a control circuit that is configured to direct the wheel to rotate a defined distance then stop to receive a container from a container queue on the conveyor. The control circuit is configured to rotate the wheel when the upper sensor confirms an upright container is in position in a receiving pocket of the wheel.

The apparatus can include a control circuit that is configured to direct the conveyor to reverse direction when a fault condition is identified based on data from at least one of the upper and lower sensors.

The apparatus can include a control circuit that is configured to direct the wheel to rotate with an empty receiving pocket to an indexed position when a fault condition associated with a fallen bottle is identified as located away from the receiving pocket based on data from the at least one lower sensor.

The containers can have a travel path that narrows in width as it approaches the wheel. The apparatus can include at least one curved upwardly extending sidewall that resides above a conveyor floor of the travel path that is concave proximate an outer perimeter of the wheel. The first lower sensor can be a retroreflective sensor.

The first and second lower sensors can be retroreflective sensors and the second lower sensor generates an optical signal that crosses the conveyor travel path a distance "D" away from the first lower sensor optical signal. In some embodiments, the distance D can be greater than one diameter but less than two diameters of the elongated containers transported by the conveyor.

The apparatus can have a container travel path that narrows in width as it approaches the wheel to a width that is less than four container diameters. The apparatus can include a control circuit that is configured to identify a "bridge" of frictionally engaged upright containers based on data from at least one of the at least one lower sensor, then automatically reverse direction of the conveyor to dislodge the bridge.

The conveyor can be substantially continuously moving during normal operation and the rotating wheel can be indexed to rotate a defined distance, then stop for receiving a container in a loading position. The apparatus comprise a control circuit that controls the indexed rotation of the wheel and can stop and/or reverse a direction of the conveyor based on data from the at least one upper and lower sensors.

The apparatus can include a control circuit that is configured to monitor the at least one upper sensor for a short interval after a fallen container fault is identified based on data from the at least one lower sensor to assess whether a container enters a receiving pocket of the wheel before generating a fallen container notification.

Yet other embodiments are directed to methods of controlling loading systems having a conveyor that merges into a rotating wheel. The methods include: (a) transmitting at least one lower optical signal across a travel path of elongated containers at a height that is below a medial portion of upright container, the at least one lower optical signal including a first optical signal that projects across a receiving pocket of a rotating wheel at a load position, the wheel having a plurality of circumferentially spaced apart receiving pockets, each pocket configured to receive one upright container at the load position; (b) concurrently transmitting at least one upper optical signal at a height that is above the at least one lower optical signal, the at least one upper optical signal configured to cross a cap portion of an upright container in the receiving pocket at the load position; (c) electronically detecting fallen containers or blockages proximate and in a receiving pocket of the wheel at the load position based on data associated with the optical signals; (d) automatically controlling a drive system associated with the wheel so that the wheel does not rotate if a fallen container is detected in the pocket of the wheel at the load position; and (e) reversing or stopping the conveyor if a bridge of abutting containers is detected proximate the wheel based on data associated with at least one of the optical signals.

The transmitting at least one lower optical signal may optionally be carried out by concurrently transmitting first and second lower optical signals across the travel path of the elongated containers so that the second optical signal is closely spaced to but does not intersect the first optical signal and is upstream of the rotating wheel.

The method may include electronically monitoring the at least one upper sensor after a fallen container fault is identified based on data from the at least one lower sensor to assess whether a container enters a receiving pocket of the wheel, then generating a fallen container notification only if an upright container has not entered the receiving pocket at the load position within about 0.5-5 seconds after a fallen container is detected based on data from the at least one lower sensor.

Still other embodiments are directed to computer program products for controlling a container transport and/or loading device. The computer program product includes a non-transitory computer readable storage medium having computer readable program code embodied in the medium. The computer-readable program code includes: (a) computer readable program code configured to monitor at least one lower optical signal including a first optical signal transmitted across a travel path of elongated containers at a height that is below a medial portion of upright container so that the first optical signal projects across a receiving pocket of a rotating wheel at a load position, the wheel having a plurality of circumferentially spaced apart receiving pockets, each pocket configured to receive one upright container at the load position; (b) computer readable program code configured to monitor at least one upper optical signal that is transmitted at a height that is above the first optical signal, the upper optical signal configured to cross a cap portion of an upright container in the receiving pocket at the load position; (c) computer readable program code configured to identify fallen containers and/or blockages proximate and in the receiving pocket of the wheel at the load position based on data associated with the optical signals; (d) computer readable program code configured to control a drive system associated with the wheel so that the wheel does not rotate if a fallen container is identified as being in a pocket of the wheel; and (e) computer readable program code configured to reverse or stop a conveyor that moves containers toward the rotating wheel if a bridge of abutting containers is detected proximate the wheel based on data associated with at least one of the optical signals.

The computer readable program code that monitors the at least one lower optical signal can be configured to monitor a second optical signal that is transmitted across the travel path of the elongated containers so that the second optical signal is closely spaced to but does not intersect the first optical signal and resides upstream of the rotating wheel.

The computer program product can include computer readable program code configured to monitor the at least one upper sensor after a fallen container fault is identified based on data from the at least one lower sensor to assess whether a container enters a receiving pocket of the wheel, then generate a fallen container notification only if an upright container has not entered the receiving pocket at the load position within about 0.5-5 seconds after a fallen container is detected based on data from the at least one lower sensor.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIGS. 11A-11K are digital images of the loading system of FIG. 2 with different fault conditions with correlated sensor indications according to embodiments of the present invention.

DETAILED DESCRIPTION OF EMBODIMENTS OF THE INVENTION

Figure 1:
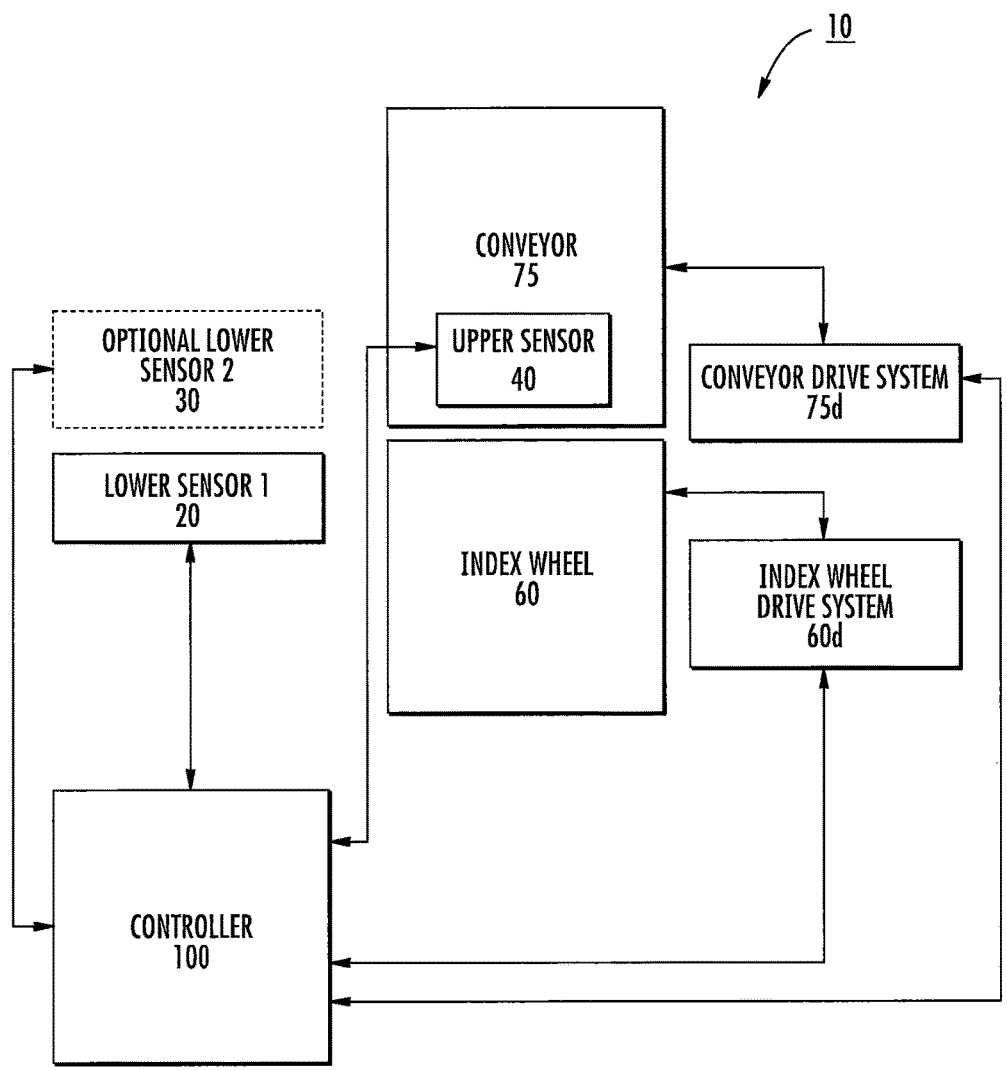
FIG. 1 is a schematic illustration of a container detection system according to embodiments of the present invention.

The present invention will now be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the thickness of certain lines, layers, components, elements or features may be exaggerated for clarity. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. The phrase "in communication with" refers to direct and indirect communication. Although described or shown with respect to one embodiment, the features so described or shown can apply to other embodiments.

In the description of embodiments of the present invention that follows, certain terms are employed to refer to the positional relationship of certain structures relative to other structures. As used herein, the term "front" or "forward" and derivatives thereof refer to the general or primary direction that a container travels to enter a test or evaluation apparatus; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the directions opposite, respectively, the forward and downstream directions.

Embodiments of the invention can use any suitable optical sensor. The term "retroreflective sensor" refers to sensors that contain both emitter and receiver elements. As is well-known to those of skill in the art, the effective beam is established between the emitter, the reflector, and the receiver. An object can be sensed when it interrupts or "breaks" the effective beam. The term "photoelectric proximity sensor" refers to sensors that transmit light in a single direction which reflects off an object in order to reach a receiver. The term "about" means that the recited number can vary, typically by +/−20%. The term "optically transmissive" refers to translucent or transparent materials.

The term "circuit" refers to software embodiments or embodiments combining software and hardware aspects, features and/or components, including, for example, at least one processor and software associated therewith (which may be provided as separate modules or as an omnibus program) embedded therein and/or executable by and/or one or more Application Specific Integrated Circuits (ASICs), for programmatically directing and/or performing certain described actions, operations or method steps. The circuit can reside in one location or multiple locations, it may be integrated into one component or may be distributed, e.g., it may reside entirely in a workstation or single computer, partially in one workstation, cabinet, or computer, or partially or totally in a remote location away from a local display at a workstation. If the latter, a local computer and/or processor can communicate over a LAN, WAN and/or internet to transmit an alert to a user of a misfeed or fallen container via the test system display, or a mobile communication device such as a cellular telephone, or electronic tablet or notepad or other computer.

The term "automatically" means that the operation can be substantially, and typically entirely, carried out without human or manual input, and is typically programmatically directed or carried out. The term "electronically" includes both wireless and wired connections between components.

FIGS. 1-4 illustrate a transport and/or loading system 10 that includes at least one lower sensor 20, shown as a first lower sensor 20, and an optional second lower sensor 30. The system 10 also includes at least one upper sensor 40, which for clarity in the description can be identified as a third sensor 40. Each sensor 20, 40 is configured to transmit a respective optical signal, 20s, 40s, and, where used, 30s.

Figure 11A:
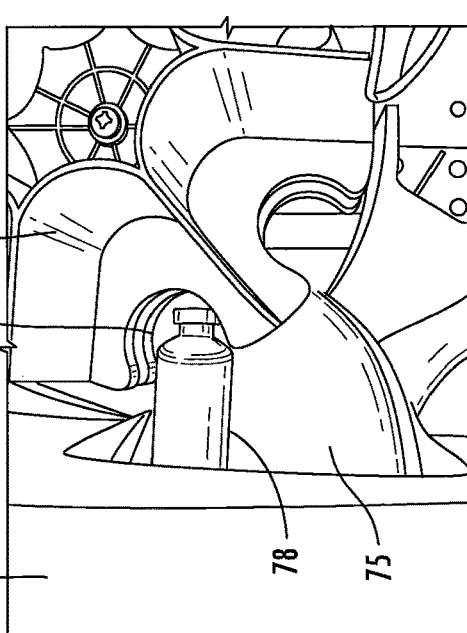
Figure 11B:
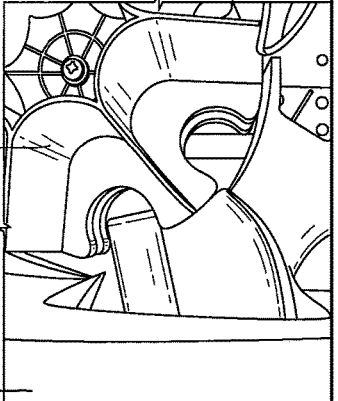
Figure 11C:
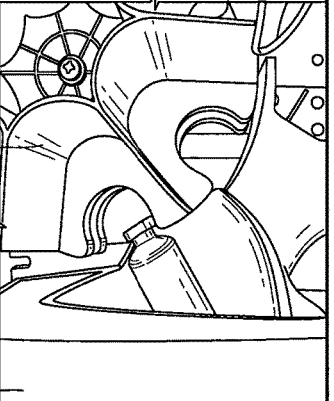
Figure 11H:
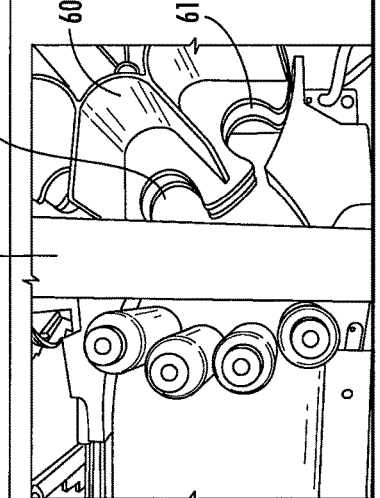
Figure 11I:
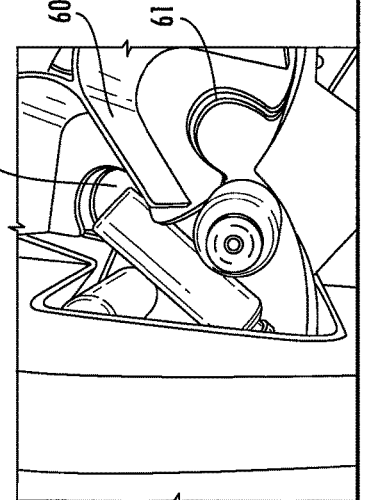

There may be one or more than one sensor (e.g., stacked or closely spaced sensors for each noted at least one lower and at least one upper sensor) for redundancy that transmits a respective signal 20s, 40s, but typically a single sensor for each respective signal is all that is required. As shown in FIG. 2B, the at least one lower sensor 20 and the at least one upper sensor 40 can project respective optical signals at different heights 20s, 40s.

Where used, the optional second lower sensor 30 may be particularly helpful in identifying bridge conditions (FIG. 11H) for some particular container travel path and container configurations.

The system 10 can include a conveyor 75 and a rotating wheel 60 with container receiving pockets 61. Each pocket 61 can be sized and configured to hold one upright container 50. The conveyor 75 has a drive system 75d and during normal operation can be configured to substantially continually move at a defined rate of speed. The wheel 60 can also have a drive system 60d. The speed of either or both drive systems 75d, 60d may be adjustable, either automatically and/or via a user depending on the number of samples being processed, container traffic at the wheel or other fault or processing conditions. The drive systems 75d, 60d can be any suitable drive system including, but not limited to, electric motors with belts, chains, or other mechanisms.

Figure 2A:
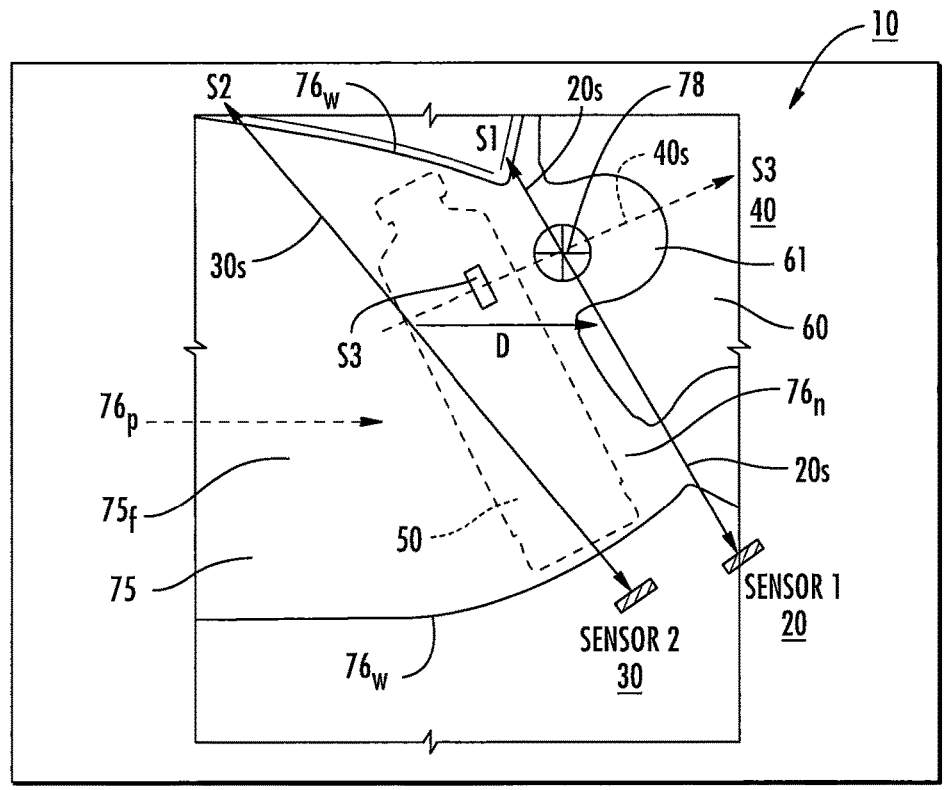
FIG. 2A is top view of a portion of a loading system showing exemplary optical signals with respect to an index wheel junction according to embodiments of the present invention.
Figure 2B:
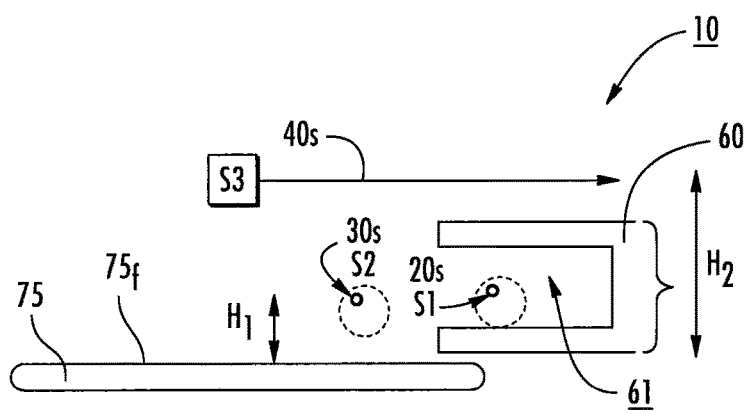
FIG. 2B is a side view of the system shown in FIG. 2A illustrating exemplary optical signal heights according to embodiments of the present invention.

As shown in FIG. 2A, the conveyor 75 can define at least a portion of a travel path 76p for concurrently transporting a plurality of containers 50 toward the wheel 60 for loading. The containers 50 can be transported concurrently for serial loading into a respective pocket 61 of the wheel 60. The containers 50 are typically elongated containers with an outermost width dimension (W) being less than a height dimension (H). In some embodiments, the height (H) is greater than twice the width (W) H>2W. In some embodiments, the containers 50 have tubular bodies with maximum outer diameters between about 1-2 inches and heights of between about 2-5 inches. Typically, the containers 50 have an outer diameter of about 1.36 inches (34.6 mm) and a height that is about 4.68 inches (119 mm).

Figure 3A:
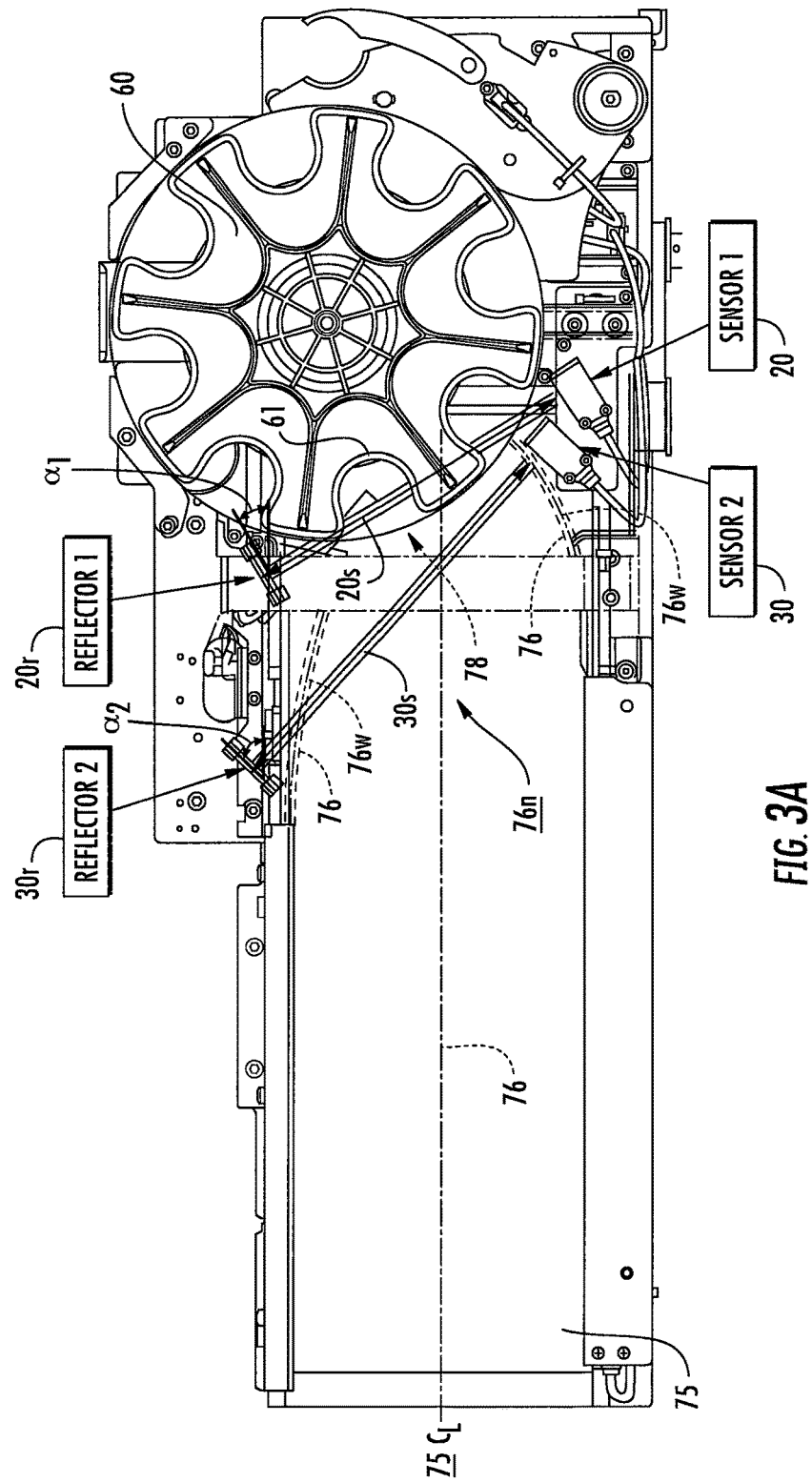
FIGS. 3A and 3B are top views of a portion of a loading system showing exemplary sensor positions according to embodiments of the present invention.
Figure 3B:
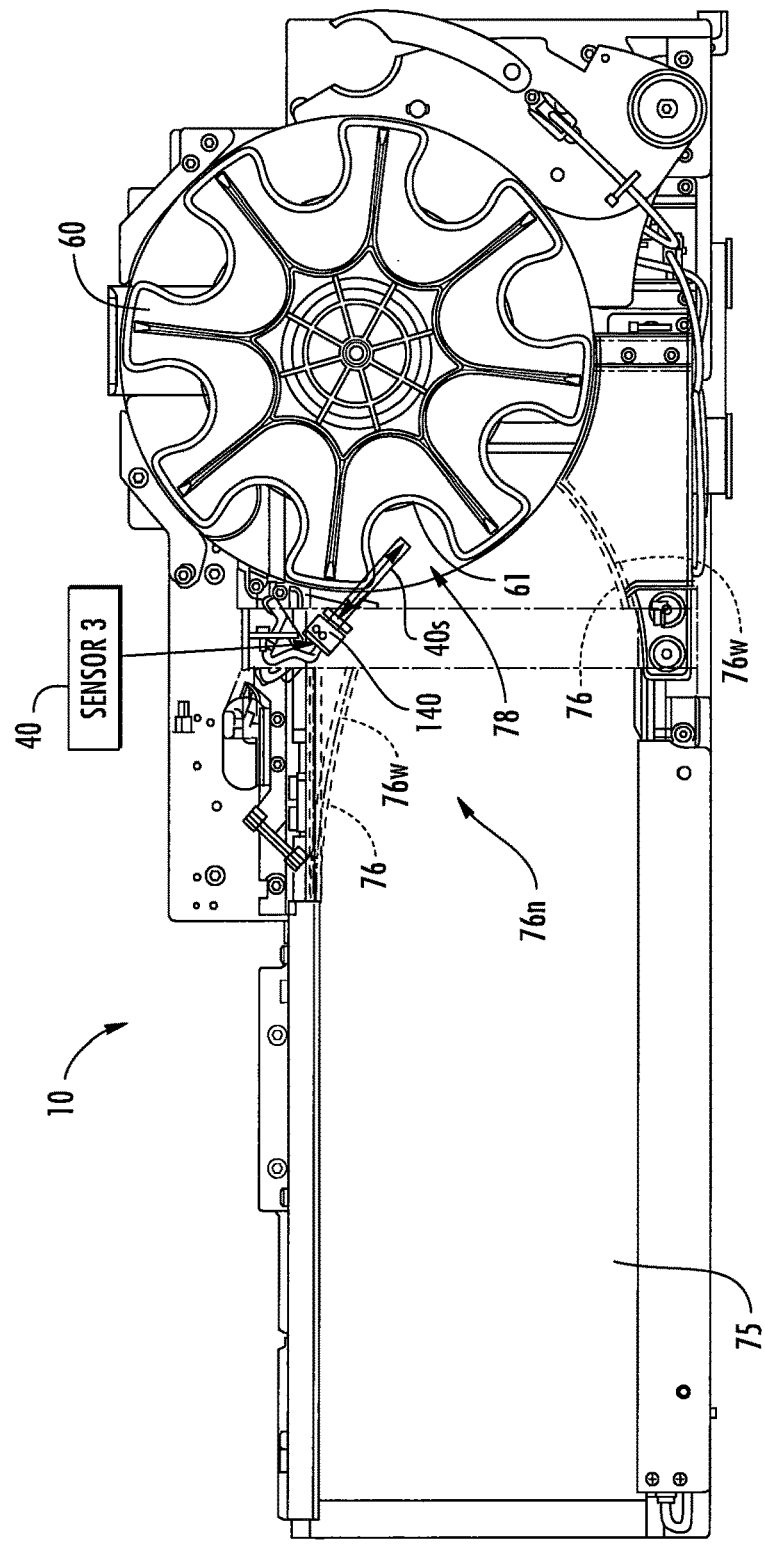

The travel path 76 can have a portion that is narrow 76n proximate an outer perimeter of the wheel 60 proximate the loading position 78 (shown schematically with an X inside a circle in FIG. 2A). As shown in FIGS. 2A, 3A and 3B (see also, FIGS. 11A-11K), the narrow portion of the travel path 76n can include curved sidewalls 76w that reside above the conveyor floor. In some particular embodiments, the narrow portion 76n of the travel path 76 can have a width that is about a length of a container 50. In some particular embodiments, the conveyor floor 75f can have a width that accommodates five (5) or more upright containers 50, then transitions to the narrow portion 76n that accommodates only four (4) or only three (3) upright containers 50. However, other configurations and/or dimensions may be suitable for some applications.

As shown in FIGS. 2A and 3A, the first lower sensor 20 and optional second lower second sensor 30 can transmit their respective optical signals across the travel path 76 of the containers 50 proximate and upstream of the wheel 60. Where both lower sensors 20, 30 are used, the two signals 20s, 30s can diverge to widen as they travel across the path 76. In other embodiments, the signals 20s, 30s may narrow or be parallel.

As shown in FIG. 2B, signal 20s and optional signal 30s can be at a relatively low height $H_1$, preferably at a distance that is below a medial portion of the container height, and typically at a location that is no greater than an outer diameter or cross-sectional transverse width of the container. This allows the optical signals 20s to detect containers that have fallen down on their sides. Although shown at the same level or height, these two signals 20s, 30s can be at different heights.

FIG. 3A illustrates that the at least one lower sensor 20 (and optionally sensor 30) can be a retroreflective sensor and, as such, the sensor 20 (and optional sensor 30) can reside on one side of the travel path 76 proximate the wheel 60 and a corresponding reflector 20r (and optional 30r), can reside on an opposite side. Suitable sensors are available from Sick AG (Germany) having a place of business as Sick, Inc., Minneapolis, Minn., Sensor Part Number WLG4S-3E1134, reflector Part Number: PL10F.

The reflectors 20r, 30r can be angled ($\alpha1$, $\alpha2$) between about 10-60 degrees from a horizontal line drawn through the reflector body that is parallel to an axially extending centerline of the travel path 76 and/or conveyor 75. As shown, the first sensor reflector 20r can be oriented with an angle of inclination $\alpha1$ that is less than the angle of inclination of the $\alpha2$ second sensor reflector 30r. In some embodiments, the first reflector 20r resides at an angle $\alpha1$ of between about 15-35 degrees while the second reflector resides at an angle $\alpha2$ of between about 30-50 degrees. In some particular embodiments, the first reflector 20r resides at an angle $\alpha1$ of about 31 degrees. Where used, in some particular embodiments, the second reflector 30r resides at an angle $\alpha2$ of about 47.5 degrees. In some embodiments, the first signal 20s is configured to extend through an outer (front) portion of a receiving pocket 61 in the loading position 78 as shown in FIGS. 2A and 3A. This signal 20s may be projected to cross other portions of a respective pocket 61 at the loading position. In some embodiments, the signal 20s can be configured to be tangential to a circular line drawn about an outer perimeter of the wheel across the pocket 61 while in other embodiments, the signal can intersect and extend across an interior portion of the pocket 61.

Where used, the second signal 30s can extend a distance "D" away from the outer edge of the pocket 61, typically between about 1 or 2 times the outer diameter of the container 50 at the minima or maxima width.

Figure 4:
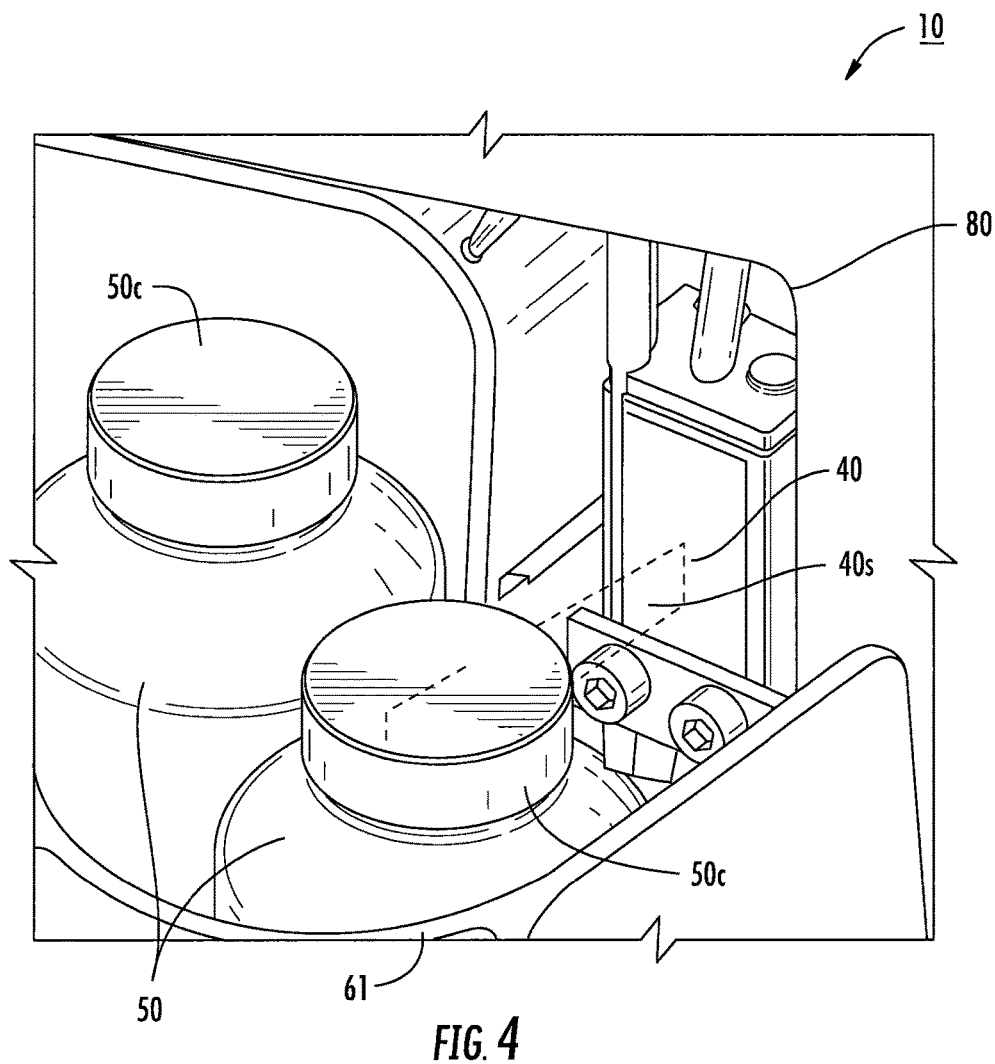
FIG. 4 is a side perspective view of the system shown in FIG. 3B illustrating an exemplary sensor location for sensor three according to embodiments of the present invention.

FIGS. 2A, 2B, 3B, and 4 illustrate the at least one upper (e.g., third) sensor 40 and associated signal 40s. Suitable sensors 40 include Part No. WTB4-3N1164 also from Sick, Inc. As shown in FIGS. 2B and 4, the third optical signal 40s is at a height ("$H_2$") that is above the height $H_1$ of the first and second signal 20s with a height that corresponds to a cap region or upper portion of 50c of an upright container to confirm that an upright container 50 is in position in a pocket 61 at the load position 78. This signal can be monitored with the other sensor signal 20s (and optional signal 30s) to allow the system or a controller 100 (FIG. 1) to index the wheel 60. The controller 100 can move the wheel 60 if the pocket 61 in the load position 78 is empty if no fallen container occludes the pocket 61 to allow already loaded containers held by the wheel 60 to be processed.

In some embodiments, if a container 50 starts to enter the wheel 60 (indexer), the container 50 may be erroneously detected as a fallen bottle initially. This may occur where an upright container 50 has not completely loaded into the pocket 61 of the wheel 60. In this situation the upper sensor 40 may not properly detect the top portion of the container 50. For this reason, when a fallen container is detected (for example, sensor 20 is triggered, but not the upper sensor 40), the fallen container detection controller 100 can be configured to wait for a fixed amount of time (short delay) to assess if the container does properly load, before a fallen container is reported. This delay allows adequate time for the container 50 to fully move into the pocket of the wheel 61 to index the wheel, thereby avoiding a "false" fallen bottle detection or inadvertent process delay for loaded containers and the like. Thus, when sensor 20 is triggered and upper sensor 40 is not, the controller 100 can be configured to poll or monitor the sensor 40 for between about 10 ms to about 5 seconds, typically between about 0.5 seconds to about 3 seconds, before generating the alert or fallen container notification.

In some embodiments, if the at least one lower sensor, e.g., either or both sensor signals 20s, 30s, indicate a blockage of frictionally engaged containers 50 (FIG. 11H), the wheel 60 can index and the conveyor 75 can be moved in a reverse direction to disrupt the blockade. The controller 100 can be configured to prevent the wheel 60 from indexing if the sensor signal 40s indicates there is no upright container in the receiving pocket 61, but one or both of sensor signals 20s, 30s indicates that there is a portion of a fallen container that extends into the pocket 61 (see, e.g., FIGS. 11A-11D).

The upper sensor 40 can be mounted and in a number of different ways and can reside in a number of different locations. The sensor 40 can be configured to generate unidirectional or bidirectional signals. As shown in FIG. 3B, for example, the sensor 40 can be mounted to a mounting member 140 that resides upstream of the wheel 60 a short distance (e.g., about 1-4 inches from the entrance of the pocket 61) and may transmit a unidirectional signal 40s toward the wheel 60. The mounting member 140 can be stationary or may be movable side to side and/or up and down.

As shown in FIG. 4, the sensor 40 can be is mounted to a bridge 80 that has a region that resides over a portion of the conveyor floor so that the sensor 40 transmits a signal 40s that is in line with an upright container in the receiving pocket 61 at the loading position 78. In some embodiments, the third sensor 40 can be mounted to a side of the conveyor 75.

Figure 5:
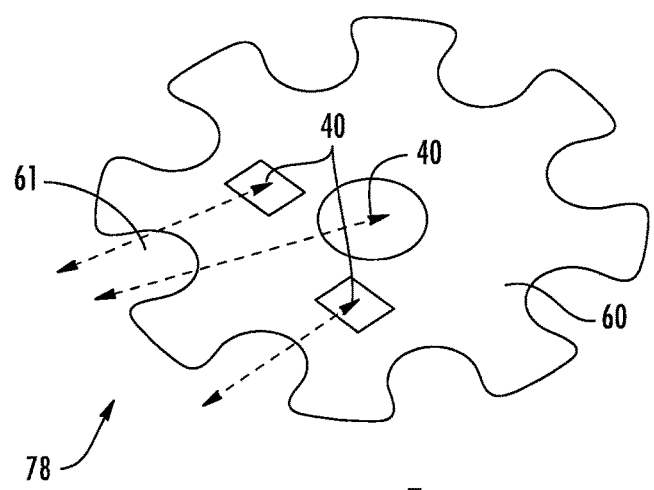
FIG. 5 is a top view of an index wheel with different on-board optical sensor configurations according to embodiments of the present invention.

As shown in FIG. 5, in some embodiments, the sensor 40 can be mounted to the wheel 60 and the sensor signal 40s can project outward toward the conveyor 75 at height $H_2$. Each pocket 61 can have its own sensor 40 or the sensor 40 can be mounted in the center of the wheel 60. The outwardly projecting signal 40s can be unidirectional.

In some embodiments, the first and second sensors 20, 30 can be retro-reflective sensors. In some embodiments, the upper/third sensor 40 can also be a retro-reflective sensor. In some embodiments, the third sensor is a reflective or a photoelectric proximity sensor. However, the sensors 20, 30, 40 can comprise other optical sensor configurations.

The system 10 can also include a controller 100 as shown in FIG. 1, for example. Generally stated, the controller 100 can direct operation of the drive systems 60d, 75d based on data from one or more of the sensors 20, 30, 40 to allow the wheel 60 to index or to prevent the wheel from indexing and/or to stop or reverse the direction of the conveyor floor. The system 10 can include additional sensors (not shown), but typically only requires the at least one lower and the at least one upper sensors 20, 40 shown for fault detection for fallen or misoriented containers at the intake zone and/or loading position 78 proximate (and at) a pocket of the wheel (see, e.g., FIGS. 11A-11K). The sensors 20 and 40 (and optional 30) can allow automated control of the conveyor floor 75 and index wheel 60 for efficient processing to reduce downtime associated with equipment malfunction due to jammed or fallen bottles.

The term "index" with reference to the word "wheel" means that the wheel can be configured to repeatedly start, then stop to move a defined distance as a respective pocket 61 rotates about a rotational cycle to serially present respective adjacent pockets at a loading position 78. This indexing can be used to present loaded pockets to one or more downstream processing stations proximate an outer perimeter portion of the wheel 60 away from the container intake zone and/or loading position 78. In some embodiments, a respective container 50 can be rotated through a series of defined workstations such as an electronic reading and/or weighing station, then to an intake port to serially move the containers 50 into a housing 200, FIGS. 7, 8 for further processing, such as, by way of example, for incubation in a climate controlled chamber, then for analysis by an automated analyzer for microbial growth and/or other defined parameters.

Figure 7:
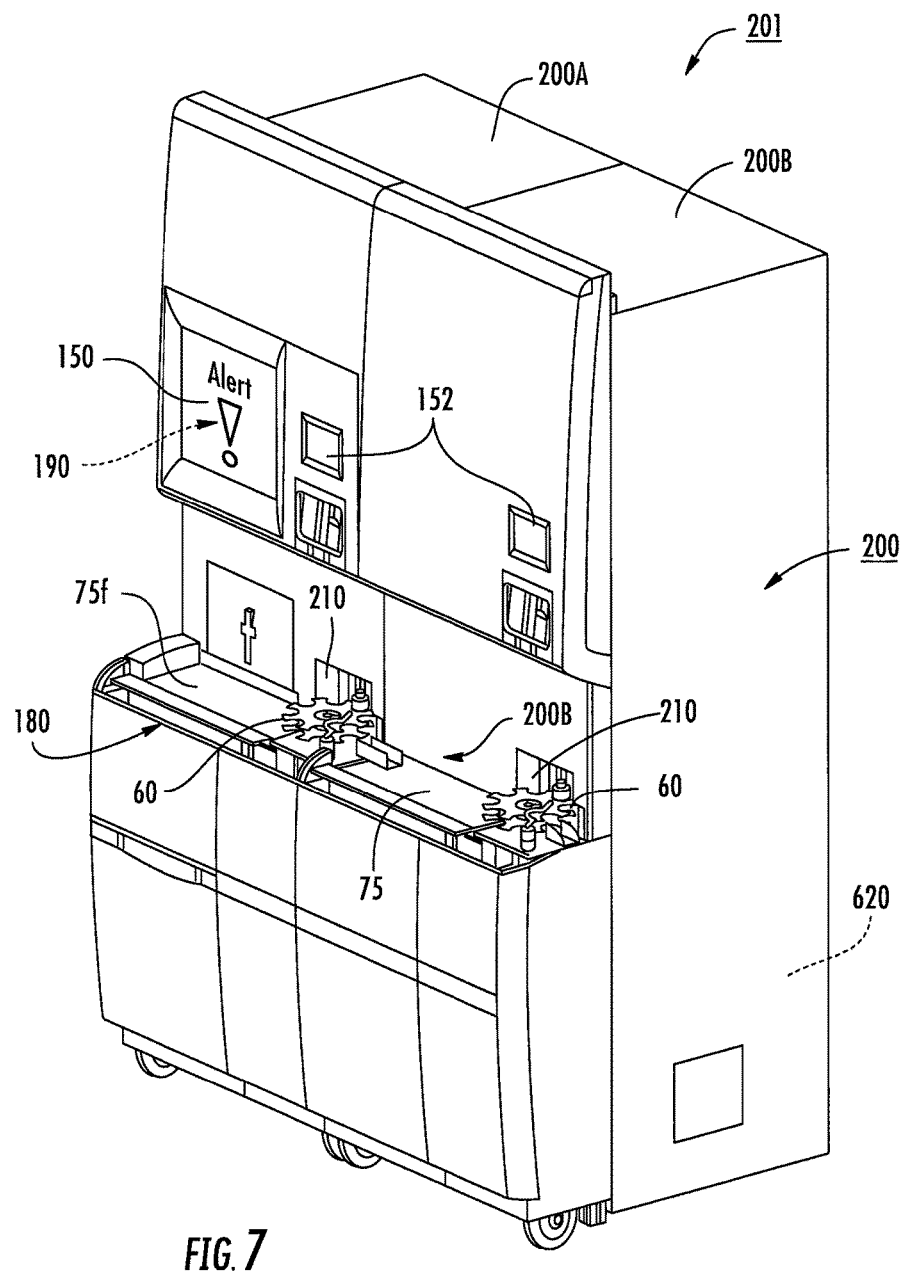
FIG. 7 is a side perspective view of an automated apparatus that uses the container detection system according to embodiments of the present invention.
Figure 8:
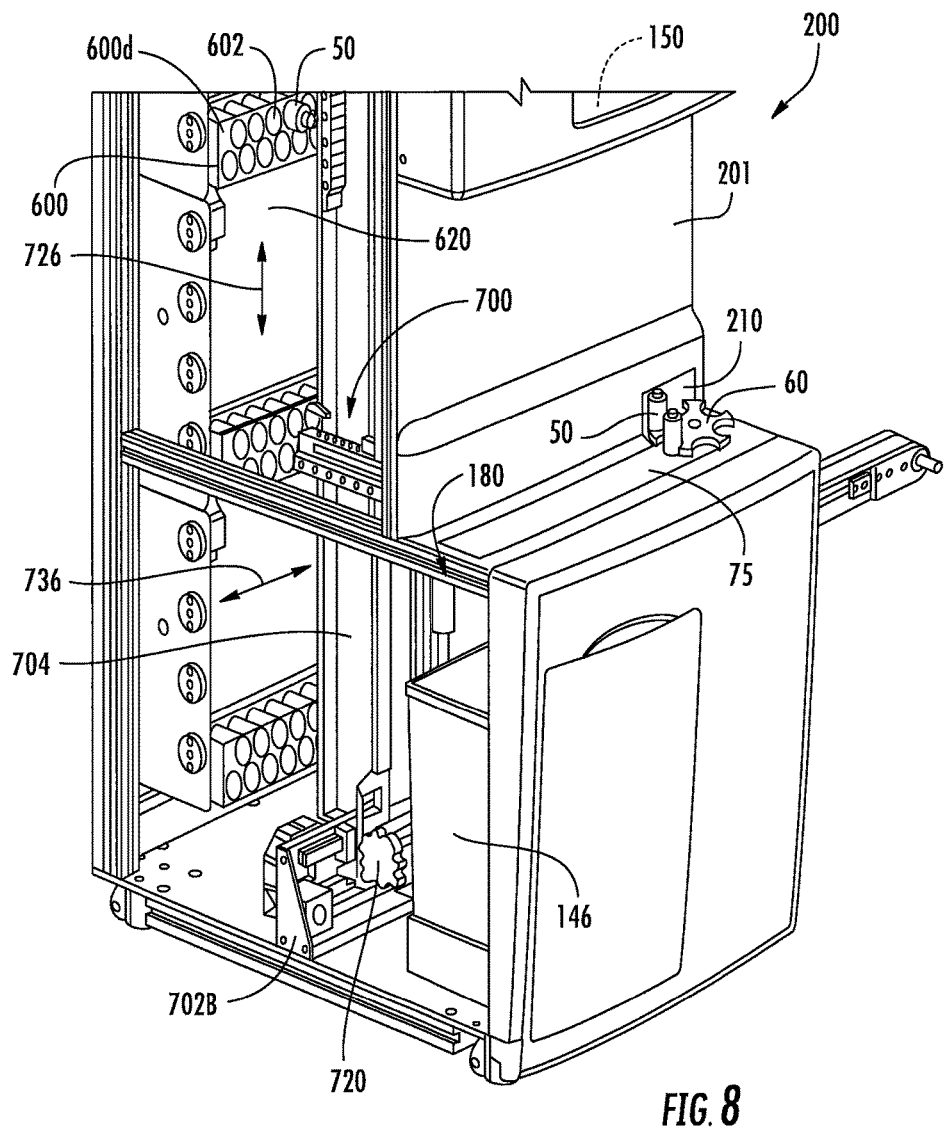
FIG. 8 is a partial cutaway view of an automated apparatus that uses a container detection system according to embodiments of the present invention.

The container detection system 10 can be particularly useful for an automated apparatus 200 such as shown in FIGS. 7 and 8 for automated detection of a microbial agent (e.g., a microorganism) that may be present in a test sample or specimen sample. In general, any known test sample (e.g., a biological sample or specimen) can be used. For example, the test sample can be a clinical or non-clinical sample suspected of containing one or more microbial agents. Biospecimens, such as a bodily fluid, include, but are not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, blood products (e.g., platelets, serum, plasma, white blood cell fractions, etc.), donor organ or tissue samples, and the like. In one embodiment, the biological sample tested is a blood sample. Other samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, and fruit) and biowarfare samples.

As shown, for example, in FIGS. 7 and 8, the automated detection system 200 comprises a housing 201 that is in communication with the conveyor 75 and wheel 60. The housing 201 forms an enclosure, enclosing an interior chamber 620. In one embodiment, the interior chamber 620 is a climate-controlled chamber (e.g., a temperature-controlled incubation chamber wherein the temperature is maintained at approximately 37 degrees Celsius) to promote or enhance microbial growth. As shown in FIGS. 7 and 8, the housing 200 also may include a first port or container entrance location 210 and a user interface display 150. However, as one of skill in the art would appreciate other design configurations are possible.

In the embodiment shown in FIGS. 7 and 8, a larger lower section of the housing supports an externally accessible shelf 180 that provides a user workstation and/or workflow access points to the detection system 200. Furthermore, the shelf 180 may hold the detection system 10 with the conveyor 75 and wheel 60 and sensors 20, 30, 40.

In operation, a user or technician (or an automated input mechanism such as a robotic arm or side feed conveyor) can place one or more specimen containers 50 onto a container loading station or area. The conveyor 75 or other transport mechanism can transport the specimen containers 50, typically upright and in gross, to the wheel 60, and subsequently into the housing 201 of the detection system 200, thereby loading the container into the system. FIG. 8 shows that the detection system 200 can be a single housing with a single interior chamber 620 while FIG. 7 shows two side-by-side housings 200A, 200B with respective conveyors 75 and wheels 60 for processing containers 50 into different input ports 210 then into respective chambers 620.

Figure 6:
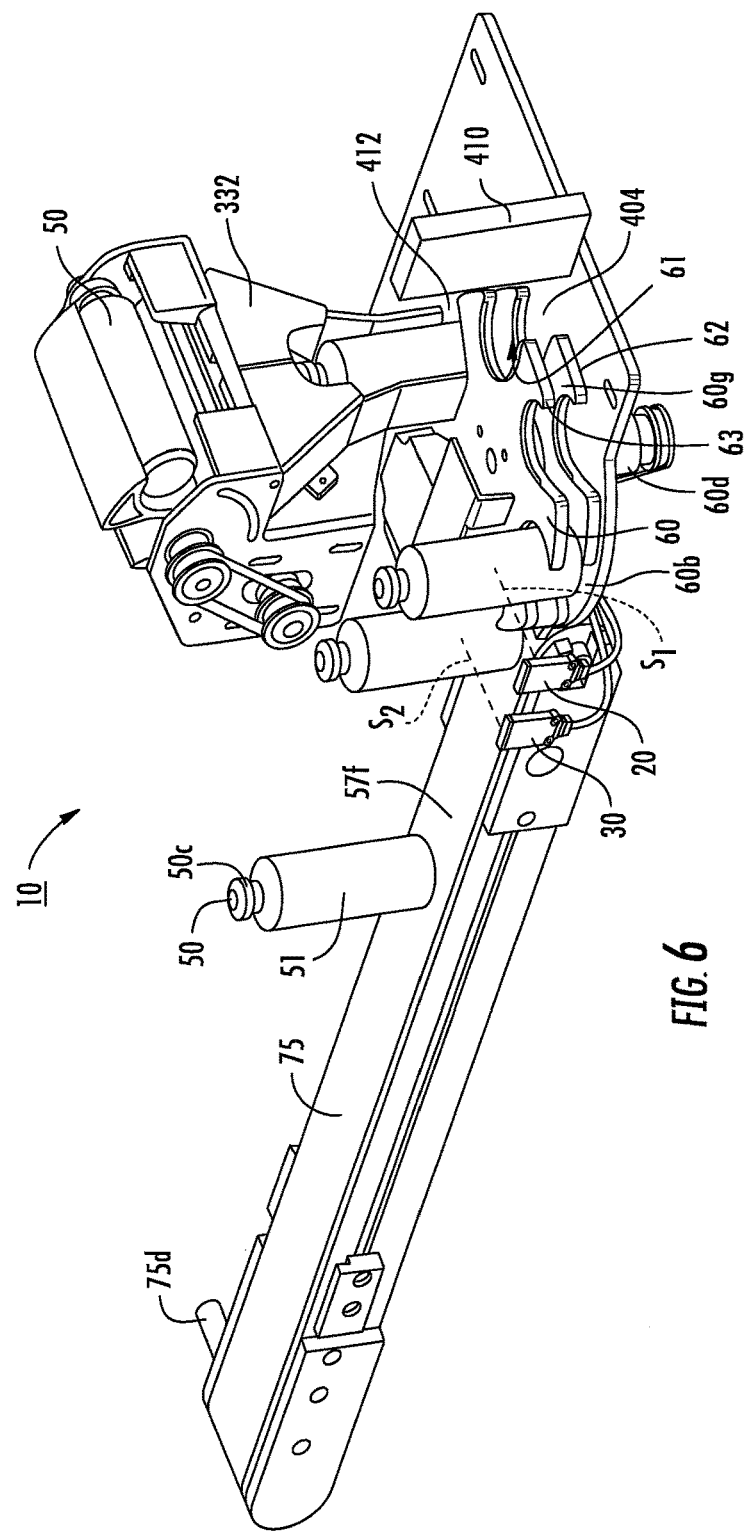
FIG. 6 is a side perspective view of an example of a container loading system according to embodiments of the present invention.

As shown for example in FIG. 6 (and described in more detail in U.S. 2011/0124028 incorporated by reference hereinabove), an automated detection system may contain one or more work-flow stations 404 for obtaining one or more measurements, readings, scans and/or images of a specimen container, thereby providing information, such as, container type, container lot number, container expiration date, patient information, sample type, test type, fill level, weight measurement, etc. FIG. 6 is shown by way of example only and not all components shown or described therewith are required and different embodiments can include different workstations or different conveyor layouts. Also, the intake configuration and the conveyor path may have different sizes, shapes and configurations, and no drum or vertical intake may be needed, for example. Furthermore, the one or more work-flow stations 404 may comprise one or more container management stations, such as a container pick-up station or a container transfer station. For example, the automated detection system may contain one or more of the following work-flow stations: (1) a bar code reading station; (2) a container scanning stations; (3) a container imaging station; (4) a container weighing station; (5) a container pick-up station; and/or (6) a container transfer station. In operation, the wheel 60 indexes to locate a specimen container 50 to one or more work-flow stations 404 positioned about the perimeter of the wheel. In some embodiments, one or more of the work-flow stations are included within the housing 201 of a respective detection system.

As shown in FIG. 6, the wheel 60 optionally communicates with a drum or drum-like loading device 308 and a vertically orientated chute 332. As shown in FIG. 6, the drum or drum-like loading device 308 rotates in a vertical plane (i.e., around or about a horizontal axis) to move the specimen container 50 from the entrance location which can direct the container to a tumbler at the top of a vertically orientated chute 332.

FIG. 6 also illustrates that the wheel 60 can define a plurality of receiving pockets 61 which can include vertically spaced apart upper and lower planar substrates 63, 62 with an open gap space 60g therebetween. The sensor 20 can project the signal 20s through the space 60g and across a front edge of a pocket 61 in the loading position.

The rotatable wheel 60 contains one or more receiving pockets 61, for example, between 1 to 20, typically between about 4-10, such as 4, 5, 6, 7, 8, 9 or 10. In operation, the wheel 60 rotates (either clockwise or counter clockwise) in a horizontal plane (and around or about a vertical axis) to move an individual container 50 to or among various work-flow stations 404 (i.e., from station-to-station). In some embodiments, the work-flow station 404 is operable to obtain one or more measurements or readings of the specimen container, thereby providing information about the container, such as, container lot number, container expiration date, patient information, sample type, fill level, etc. In some embodiments, one or more of these measurements and/or readings can occur at the same station. For example, container weight, scanning, imaging and/or pick-up may occur at a single station location.

As shown in FIG. 8, in some embodiments, the detection system 200 will also include a detector 600d for detecting growth (e.g., a detection unit) in the specimen containers 50. In general, any detector configuration or type for detecting microbial growth in a container can be used. For example, as is well known in the art, each holding station or rack 600 may contain horizontal pockets 602 and a linear scanning optical system that has the capability of non-invasive monitoring of microorganism growth in each specimen container 50. In one embodiment, the optical system detector 600d can interrogate a sensor (e.g., a Liquid Emulsion Sensor (LES) sensor) in the containers 50, thereby detecting for microorganism growth within the container.

In general, any known detection system for monitoring and/or interrogating a specimen container for the detection of microbial growth can be used. As previously mentioned, the specimen containers 50 can be monitored continuously, or periodically, during incubation of the containers 50 in the detection system 100, for the positive detection of microbial growth. For example, in one embodiment, a detection unit 600d reads the sensor 51 (FIG. 6) incorporated into a bottom portion or base of the container 50. A variety of sensor technologies are available in the art and may suitable. In one possible embodiment, the detection unit takes colorimetric measurements as described in the U.S. Pat. Nos. 4,945,060; 5,094,955; 5,162,229; 5,164,796; 5,217,876; 5,795,773; and 5,856,175, which are incorporated herein. A positive container is indicated depending upon these colorimetric measurements, as explained in these patents. Alternatively, detection could also be accomplished using intrinsic fluorescence of the microorganism, and/or detection of changes in the optical scattering of the media (as disclosed, for example, in co-pending U.S. patent application Ser. No. 12/460,607, filed Jul. 22, 2009 and entitled, "Method and System for Detection and/or Characterization of a Biological Particle in a Sample"). In yet another embodiment, detection can be accomplished by detecting or sensing the generation of volatile organic compounds in the media or headspace of the container. Various design configurations for the detection unit can be employed within the detection system. For example, one detection unit could be provided for an entire rack or tray, or multiple detection units could be provided per rack or per tray.

The specimen container 50 is shown in the form of a standard culture bottle (e.g., a blood culture bottle). However, the description of a culture bottle (e.g., a blood culture bottle) is offered by way of example and not limitation. The container 50 may include a bar code label for automated reading of the container 50. In some embodiments, the top portion of the container 50 can include a narrow portion or neck. The container 50 also includes a cap (e.g., a stopper) optionally having a pierceable septum and may also have a sensor (e.g., an LES sensor) formed or placed in the bottom portion of the container 50 for purposes of colorimetric detection of the presence of microbial growth in the container 50. The container 50 can include a body with an optically transmissive material. The container 50 may further comprise a growth or culture medium (not shown) for promoting and/or enhancing microbial or microorganism growth. The use of a growth or culture media (or medium) for the cultivation of microorganisms is well known. A suitable growth or culture medium provides the proper nutritional and environmental conditions for growth of microorganisms and should contain all the nutrients required by the microorganism which is to be cultivated in the specimen container 50. After a sufficient time interval to allow amplification of microorganisms (this time interval varies from species to species), the container 50 can be tested within the detection system 200 for the presence of microbial or microorganism growth. The testing may occur continuously or on a periodic basis so that the container can be determined as positive for microorganism growth as soon as possible.

In some embodiments, once a container 50 is detected as positive for the indication (e.g., microorganism) in the detection system 200, the system 200 can notify the operator through an indicator 190 (e.g., a visual prompt), and/or via a notification at the user interface display 150, or by other means.

The conveyor belt 75 may run continuously, or may be activated by the physical presence of a container 50 at a loading station or area. For example, a system controller 100 (FIG. 1) can be used to operate the conveyor belt 75 based on a signal (e.g., a light sensor) indicating the presence, or absence, of one or more specimen containers at the loading station if a defined fault condition does not occur based on sensors 20, 40 and optionally sensor 30.

As discussed above, for example with respect to FIGS. 2 and 11A, the conveyor communicates with one or more guide rails 76 with curved sidewalls 76w located juxtaposed to one or both sides of conveyor 75 proximate the wheel 60. The guide rails 76 can operate to funnel or guide the specimen containers into a single file line at the back of the automated loading mechanism 60, where they await their turn to be loaded, one container at a time, into the detection system 200.

As shown, for example in FIG. 8, the automated detection system 200 may further comprise an automated mechanism 700 operable for the transfer of a specimen container 50 for container management within the system. As the containers 50 accumulate in the entrance location or port 210, the containers 50 are moved within the detection system 200 whereby a transfer mechanism (e.g., a robotic transfer arm with a container grip mechanism) can pick up, or otherwise receive, an individual specimen container 50 and transfer and place that container into a holding structure or rack 600 within the detection system 200. As known in the art, the mechanism may use a vision system (e.g., camera), pre-programmed dimensional coordinates and/or precision motion controlling to transfer a specimen container to, and load the specimen container into, the holding structure or rack 600.

As shown, the containers 50 are typically loaded into the detection system 200 in a vertical orientation (i.e., such that the top or cap portion 50c of the container 50 is up-right). In accordance with one embodiment, the containers 50 are placed or held in a plurality of holding structures or racks 600, and optionally agitated to enhance microorganism growth therein. As shown for example in FIG. 8, the receiving structures or wells 602 of the holding structures or racks 600 can be orientated along a horizontal axis. Accordingly, in accordance with this embodiment, an automated transfer mechanism 700 re-orientates the containers 50, from a vertical orientation to a horizontal orientation, during the transfer of the container 50 from the wheel 60 to the holding members/rack wells 602.

In some embodiments, the transfer mechanism 700 can operate to remove or unload "positive" and "negative" containers from the holding structures or racks 600. This automated unloading mechanism can operate to ensure that once a "positive" or "negative" reading has been made for each specimen container 50, the container 50 is removed from the container receiving structures or well 602, making room for another container to be loaded into the detection system 200, thereby increasing system through-put.

In some embodiments, the transfer mechanism 700 comprise a robotic transfer arm. In general, any type of robotic transfer arm known in the art can be used. For example, the robotic transfer arm can be a multi-axis robotic arm (for example, a 2-, 3-, 4-, 5-, or 6-axis robotic arm). The robotic transfer arm can operate to pick up and transfer a specimen container 50 (e.g., a blood culture bottle) from an entrance location or port 210 to one of a plurality of container receiving structures or wells 602 located in one of a plurality of holding structures or racks 600 (optionally having an agitation assembly). Furthermore, to facilitate the movements of the transfer mechanism or robotic transfer arm, the interior chamber 620 of the detection system 200 may include one or more supports for the robotic transfer arm. For example, one or more vertical supports and/or one or more horizontal supports may be provided. The transfer mechanism or robotic transfer arm can slide up and down and across the supports as necessary to access any of the receiving structures or wells 602 of the holding structures or racks 600.

In yet another embodiment, the robotic transfer arm may include one or more devices for obtaining measurements, scans and/or readings of a specimen container 50. For example, the robotic transfer arm may include one or more video cameras, sensors, scanners, and/or bar code readers. In accordance with this embodiment, the video camera, sensor, scanner and/or bar code reader may aid in container location, reading of container labels (e.g., bar codes), container scanning, remote field servicing of the system, and/or detecting for any possible container leaks within the system. In yet another design possibility, the robotic transfer arm may include a UV light source to aid in automated decontamination, if necessary.

The transfer mechanism robotic transfer arm 700 can include one or more horizontal support structures 702B, one or more vertical support structures 704, and a robotic head that will include one or more features or devices (e.g., a gripping mechanism) to pick-up, grip and/or hold a specimen container 50. The robotic head can be supported by, coupled to, and/or attached to one of the horizontal supports and/or vertical supports. For example, as shown in FIG. 8, the robotic transfer arm 700 comprises a lower horizontal support structure 702B and a single vertical support structure 704. Although not shown, as one of skill in the art would appreciate, an upper horizontal support structure or other similar means can be used to further support or guide the vertical support structure. In general, any known means in the art can be used to move the robotic head up and down the vertical support rail 704 (as represented by arrow 726), and move the vertical support rail 704 back-and-forth along the horizontal support structure(s) 702B (as represented by arrow 736). The robotic transfer arm 700 may further comprise a vertical drive motor 720 and vertical drive belt that can operate to transfer or move the robotic head up and down (arrow 726) the vertical support rail 704 to transfer or move a container 50 along (i.e., up and down) a vertical axis (i.e., the y-axis). Accordingly, the vertical support structure 704, vertical guide rail 728, vertical drive motor 720 and vertical drive belt allow the robotic transfer arm 700 to move or transfer the robotic head and a specimen container 50 along the y-axis. The robotic transfer arm 700 may further comprise a first horizontal drive motor, first horizontal drive belt and horizontal guide rail that will operate to move the vertical support structure 704 back-and-forth (i.e., from left-to-right and/or from right-to-left) along the horizontal guide rail, and thus, along a first horizontal axis (i.e., the x-axis) within the housing 201 of the detection system 200 (see arrow 736). Accordingly, the robotic transfer arm 700 move or transfer a specimen container 50 along the x-axis. The automated robotic transfer arm 700 can be placed under the control of a system controller (100, FIG. 1) and programmed for specimen container 50 management (e.g., pick-up, transfer, placement and/or container removal) within the detection system 200.

As shown in FIG. 8, there can be a plurality of vertically stacked container holding structures or racks 600, each having a multitude of specimen container receiving structures or wells 602, each for holding individual specimen containers 50 inside chamber 620. Each individual holding structure or rack 600 can comprise two or more container receiving structures of wells 602. For example, each holding structure or rack 600 can comprise from about 2 to about 40, from about 2 to about 30, or from about 2 to about 20 receiving structures of wells 602 therein. In one embodiment, as shown in FIG. 8, the racks 600 can comprise 2 rows of vertically aligned receiving structures or wells 602. In an alternative embodiment, the receiving structures or wells 602 can be staggered, thus reducing the vertical height of each individual holding structure or rack 600, thereby allowing for an increased number of total holding structures or racks 600 in a given vertical distance within the incubation chamber 620.

Furthermore, each of the individual container receiving structures or wells 602 has a specific X and Y coordinate position or address, where X is the horizontal location and Y is the vertical location of each container receiving structure or well 602. The individual wells 602 are accessed by a transfer mechanism, such as a robotic transfer arm 700, for example, as described hereinabove. The automated transfer mechanism 700 can operate to move the robotic head with a respective specimen container 50, to a specific of the X, Y positions in the rack 600 and deposit the container 50 therein. In operation, the automated transfer mechanism 700 can operate to pick-up a specimen container 50 at the entrance station 210 or other pick-up station, move a container 50 determined positive for microbial growth therein to a positive container or exit location and/or to move a container 50 determined negative for microbial growth to a negative container location or waste bin 146 (FIG. 8).

In some embodiments, the entire holding structure or rack 600 can be agitated by an agitation assembly (not shown) to promote or enhance microorganism growth. The agitation assembly can be any known means or mechanism for providing agitation (e.g., a back-and-forth rocking motion) to the holding structures or racks 600. In another embodiment, the holding structures or racks 600 can be rocked in a back-and-forth motion for agitation of the fluid contained within the containers. For example, the holding structures or racks 600 can be rocked back-and-forth from a substantially vertical position to a substantially horizontal position, and repeated to provide agitation of the fluid contained within the container. In yet another embodiment, the holding structures or racks 600 can be rocked back-and-forth from a substantially horizontal position to a vertical position 10 degrees, 15 degrees, 30 degrees, 45 degrees or 60 degrees from horizontal, and repeated to provide fluid agitation within the containers. In one embodiment, a racking motion from a substantially horizontal position to a vertical position from about 10 degrees to about 15 degrees from horizontal may be preferred. In still another embodiment, the holding structure or racks can be rocked back-and-forth in a linear or horizontal motion to provide agitation of the fluid contained within the containers. In this embodiment, the holding structures or racks 600 and receiving structures or wells 602 can be orientated in a vertical, or alternatively in a horizontal position. These back-and-forth, liner and/or horizontal rocking motions can be repeated as desired (e.g., at various cycles and/or speeds) to provide agitation of the fluid within the containers.

As previously described, the detection system 200 may include a climate-controlled interior chamber (or incubation chamber) 620 for maintaining an environment to promote and/or enhance growth of any microbial agents (e.g., microorganisms) that may be present in the specimen container 50. In accordance with this embodiment, the detection system 200 may include a heating element or hot air blower to maintain a constant temperature within said interior chamber. For example, in one embodiment, the heating element or hot air blower will provide and/or maintain the interior chamber at an elevated temperature (i.e., a temperature elevated above room temperature). In another embodiment, the detection system may include a cooling element or cold air blower (not shown) to maintain the interior chamber at a temperature below room temperature. In accordance with this embodiment, the interior chamber or incubation chamber will be at a temperature of from about 18 to about 45 degrees Celsius. In one embodiment, the interior chamber can be an incubation chamber and can be maintained at a temperature from about 35 degrees Celsius to about 40 degrees Celsius, and preferably at about 37 degrees Celsius. In another embodiment, the interior chamber may be maintained at a temperature below room temperature, for example from about 18 degrees Celsius to about 25 degrees Celsius, and preferably at about 22.5 degrees Celsius. A particular advantage provided is the ability to provide a more constant temperature environment for promoting and/or enhancing microbial growth within a specimen container 50. The detection system 200 can accomplish this by providing a closed system, in which automated loading, transfer and unloading of specimen containers 50 occurs without the need to open any access panels that would otherwise disrupt the incubation temperature (from about 30 to 40 degrees Celsius, preferably from about 37 degrees Celsius) of the interior chamber 620.

The detection system 200 can employ any known means in the art for maintaining a climate-controlled chamber for promoting or enhancing microbial growth. For example, to maintain a temperature controlled chamber, one or more heating element or hot air blower, baffles and/or other suitable equipment known in the art, can be used to maintain the interior of the detection system 200 at the appropriate temperature for incubating the container and promoting and/or enhancing microbial growth. Typically, one or more heating elements and/or hot air blowers under control of the system controller 100 (FIG. 1) are used to maintain a constant temperature within the interior chamber 620 of the detection system 200. As known in the art, the heating element or hot air blower can be employed in a number of locations within the interior chamber. For example, one or more heating elements or hot air blowers can be positioned at the base of the holding structures or racks 600, for directing warm air across the plurality of holding structures or racks 600.

The detection system 200 will include a system controller (e.g., a computer control system) (100, FIG. 1) and firmware for controlling the various operations and mechanisms of the system. Typically, the system controller and firmware for controlling the operation of the various mechanisms of the system can be any known conventional controller and firmware known to those of skill in the art. In one embodiment, the controller and firmware can direct all operations for controlling the various mechanisms of the system, including: automated loading, automated transfer, automated detection and/or automated unloading of specimen containers within the system. The controller and firmware can also provide for identification and tracking of specimen containers within the system.

The detection system 200 may also include a user interface 150 and associated computer control system for operating the loading mechanism, transfer mechanism, racks, agitation equipment, incubation apparatus, and receiving measurements from the detection units. The user interface 150 may also provide an operator or laboratory technician with status information regarding containers loaded into the detection system. The user interface may includes one or more of the following features: (1) Touch screen display; (2)

Keyboard on touch screen; (3) System status; (4) Positives alert; (5) Communications to other systems (DMS, LIS, BCES & other detection or identification Instruments); (6) Container or bottle status; (7) Retrieve containers or bottles; (8) Visual and audible Positive Indicator; (9) USB access (back ups and external system access); and (10) Remote Notification of Positives, System Status and Error Messages. In another embodiment, as shown in FIG. 7, a status update screen 152 can also be used. The status update screen 152 can be used to provide status information regarding containers loaded into the detection system, such as, for example: (1) container location within the system; (2) container information, such as, patient information, sample type, input time, etc.; (3) positive or negative container alerts; (4) interior chamber temperature; and (5) an indication that the waste bin is full and needs to be emptied.

Once a container is detected as positive, the detection system will notify the operator of the results through an indicator (e.g. visual prompt 190, FIG. 7) and/or through notification at the user interface 150 or even other defined portable communication devices (remote and/or local).

As noted above, the detection system 200 can take on a variety of different possible configurations. One such configuration, particularly suited for high volume implementations, is for use as an automated microbiology laboratory system. For example, the detection instrument 200 can be included as one component of an automated laboratory system. In this embodiment, the detection instrument 200 can be linked or "daisy chained" to one or more additional other analytical modules or instruments for additional testing. For example, as shown in FIG. 7, the detection instrument can include a plurality of adjacent (abutting) units, such as a first detection unit 200A and a second detection unit 100B. However, in other embodiments, the detection instrument can be "daisy chained" or otherwise linked to one or more other systems or modules. These other systems or modules can include, for example, identification testing systems such as the VITEK or VIDAS systems of the assignee bioMerieux, Inc., a gram stainer, a mass spectrometry unit, a molecular diagnostic test system, a plate streaker, an automated characterization and/or identification system (as disclosed in U.S. patent application No. 60/216,339, entitled "System for Rapid Non-invasive Detection of a Microbial Agent in a Biological Sample and Identifying and/or Characterizing the Microbial Agent", which was filed May 15, 2009) or other analytical systems.

Respective containers can be transferred from one detection system to another (e.g., in case the first one is full). A transfer device may also be provided for subsequent transfer of the specimen container 500 from the second detection system 200B to a subsequent systems or modules. Further, in accordance with this embodiment, positive containers can be transferred to other systems in the automated laboratory system. For example, a container determined positive in the first detection system 200A can be transferred to the second detection system 200B and/or subsequently to an automated characterization/identification system (not shown) for automated characterization and/or identification of the microbe therein. As one of skill in the art would appreciate other possible designs or configurations for the automated laboratory system are possible and are considered part of this invention.

As discussed above, embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means and/or implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 9:
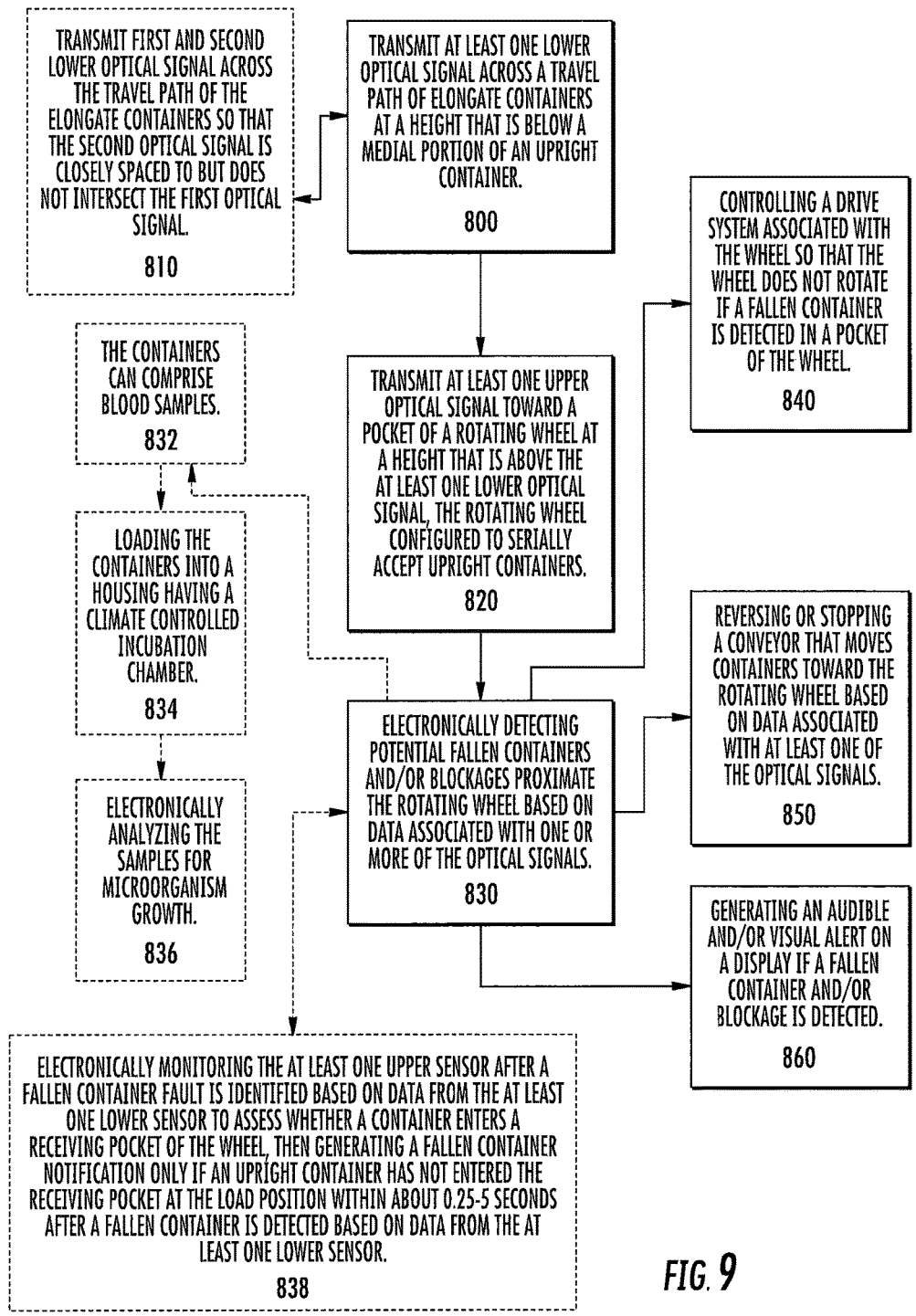
FIG. 9 is a flow chart of exemplary operations that can be used to carry out embodiments of the present invention.

FIG. 9 illustrates exemplary operations that can be used to carry out embodiments of the invention. At least one lower optical signal is transmitted across a travel path of elongated containers at a height that is below a medial portion of an upright container (block 800). The at least one transmission can optionally be carried out using first and second lower optical signals transmitted (concurrently) across the travel path of the elongated containers so that the second optical signal is closely spaced to but does not intersect the first optical signal (block 810). At least one upper optical signal is transmitted toward a pocket of a rotating wheel at a height that is above the first and second optical signals, the rotating wheel configured to serially accept upright containers (block 820). Potential fallen containers or blockages are electronically detected proximate a rotating wheel configured to serially accept upright containers based on data associated with the optical signals (block 830).

A drive system associated with the wheel can be controlled so that the wheel does not rotate if a fallen container is detected in a pocket of the wheel (block 840). A conveyor that moves containers toward the rotating wheel can be reversed or stopped based on data associated with at least one of the first, second and third optical signals (block 850). An audible and/or visual alert can be generated on a local, remote display and/or on a portable device (e.g., PDA, smartphone or electronic notebook or other device) with a display, if a fallen container or blockage is detected (block 860).

The containers can optionally comprise blood samples (block 832).

The containers can optionally be loaded into a housing having a climate controlled incubation chamber (block 834) and analyzing the samples for microorganism growth (block 836).

The method can also include electronically monitoring the at least one upper sensor after a fallen container fault is identified based on data from the at least one lower sensor to assess whether a container enters a receiving pocket of the wheel, then generating a fallen container notification only if an upright container has not entered the receiving pocket at the load position within a defined time, e.g., between about 0.25-5 seconds, typically between 0.5 to 4 seconds, after a fallen container is detected based on data from the at least one lower sensor (block 838). This action may avoid false positive notifications.

Figure 10:
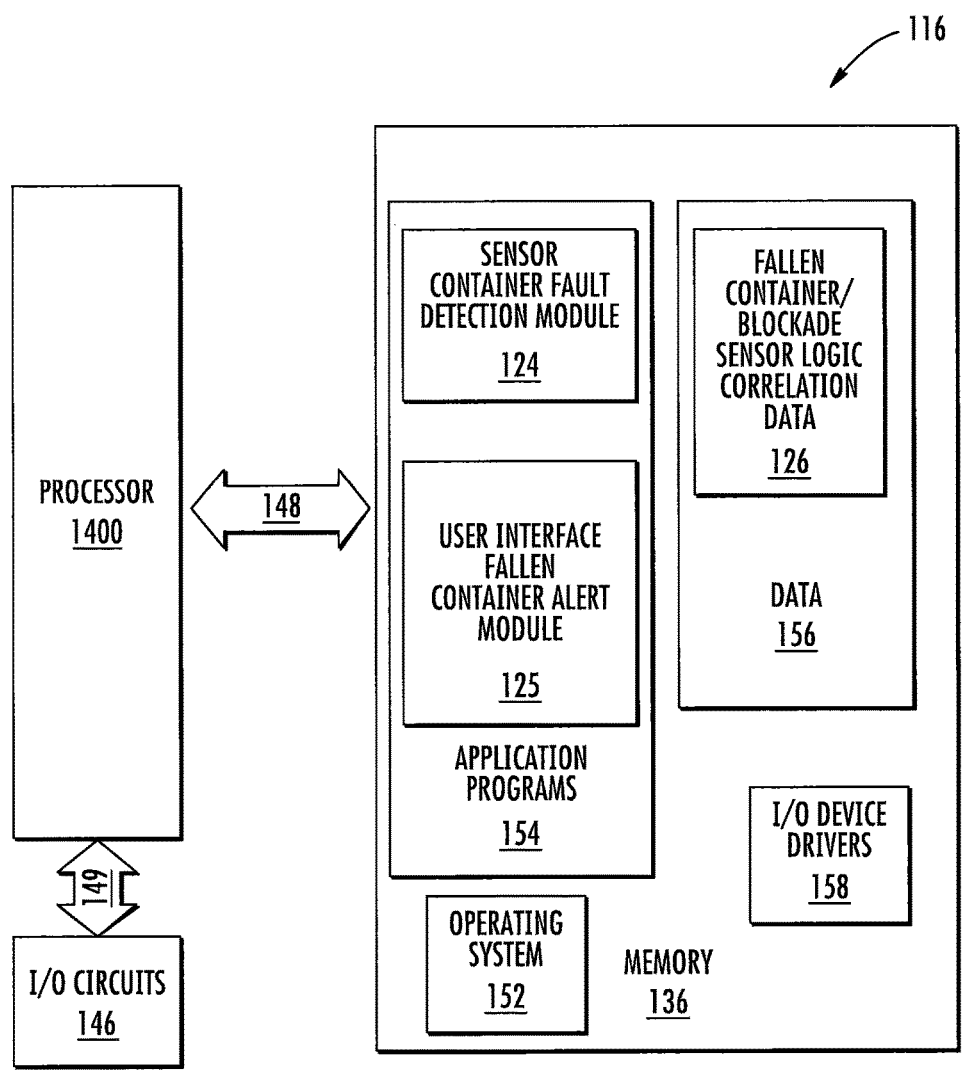
FIG. 10 is a schematic illustration of a data processing circuit or system according to some embodiments of the present invention.

The samples can optionally be electronically analyzed for microorganism growth. As illustrated in FIG. 10, embodiments of the invention may be configured as a data processing system 116, which can be used to carry out or direct operations of the rendering, and can include a processor circuit 1400, a memory 136 and input/output circuits 146. The data processing system may be incorporated in, for example, one or more of a personal computer, workstation 10w, server, router or the like. The system 116 can reside on one machine, such as in the controller 100 (FIG. 1) or be distributed over a plurality of machines. The processor 400 communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

In particular, the processor 1400 can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: ROM, PROM, EPROM, EEPROM, flash memory, SRAM, DRAM and magnetic disk. In some embodiments of the present invention, the memory 136 may be a content addressable memory (CAM).

As further illustrated in FIG. 10, the memory (and/or storage media) 136 may include several categories of software and data used in the data processing system: an operating system 152; application programs 154; input/output device drivers 158; and data 156. As will be appreciated by those of skill in the art, the operating system 152 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154 the operating system 152 the input/output device drivers 158 and other software programs that may reside in the memory 136.

The data 156 may include (archived or stored) fallen container/sensor correlation and/or logic fault condition data sets 126 correlated to respective fault conditions associated with a defined set of sensor detection configurations to fallen container orientations and locations.

As further illustrated in FIG. 10, according to some embodiments of the present invention application programs 154 include a Sensor Container Fault Detection Module 124 and a User Interface Fallen Container Alert Module 125. The data interface module can be decoupled or isolated from the visualization/rendering module. The application program 154 may be located in a local server (or processor) and/or database or a remote server (or processor) and/or database, or combinations of local and remote databases and/or servers.

While the present invention is illustrated with reference to the application programs 154, and Modules 124, 125 in FIG. 10, as will be appreciated by those of skill in the art, other configurations fall within the scope of the present invention. For example, rather than being application programs 154 these circuits and modules may also be incorporated into the operating system 152 or other such logical division of the data processing system. Furthermore, while the application programs 124, 125 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 10 but may be provided by other arrangements and/or divisions of functions between data processing systems. For example, although FIG. 10 is illustrated as having various circuits and modules, one or more of these circuits or modules may be combined or separated without departing from the scope of the present invention.

FIGS. 11A-11K illustrate various "fault" conditions that can be identified using one or more of the sensors 20, 30, 40. The appended charts identify which one or sets of the monitored sensors that identify the condition shown. Sensor 40 is not indicated as identifying a particular fault, as it is used to identify an open or loaded pocket. The second lower sensor 30, e.g., sensor 2, is optional but included by way of example only in these figures. The fallen container logic can be modified so to use sensor 1 and sensor 3. This data can be used to allow the controller 100 to direct the index wheel 60 to rotate or not or to reverse the conveyor, for example.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An automated misfeed and/or fallen container detection system comprising:
    a conveyor providing a travel path for groups of elongated containers;
    a rotating wheel in cooperating alignment with the conveyor, the wheel having a plurality of circumferentially spaced apart pockets, each pocket configured to accept a single upright elongated container; and
    a plurality of spaced apart sensors including (i) at least one lower sensor configured to transmit a respective optical signal across the container travel path proximate the wheel at a height that is less than a width dimension of the containers, the at least one lower sensor including a first lower sensor that transmits a respective first optical signal across a front edge portion of a pocket of the wheel facing the conveyor at a loading position and (ii) at least one upper sensor that is positioned proximate the wheel configured to transmit an optical signal at a height corresponding to a top portion of an upright container to thereby allow detection of different orientations and positions of fallen containers and/or container jam or blockage conditions.

2. The system of claim 1, wherein the at least one lower sensor comprises a first lower sensor and a second lower sensor, the second lower sensor positioned longitudinally spaced apart from the first lower sensor, the first lower sensor being downstream of the second lower sensor, with each residing proximate the rotating wheel, wherein the first and second lower sensors configured to transmit respective first and second non-intersecting first and second optical signals across the conveyor container travel path proximate the rotating wheel at a height that is no greater than 1-2 inches associated with a width dimension of the containers.

3. The system of claim 1, further comprising a plurality of elongated containers on the conveyor, wherein the containers are optically transmissive tubes with a top cap, and the containers have one size with an outer diameter, wherein the at least one lower sensor is positioned to transmit a respective optical signal at a height that is no greater than the diameter of the containers.

4. The system of claim 2, wherein the first and second lower sensors have optical signals that diverge away from each other as they project across the conveyor so that the first and second optical signals are closer together on one side of the conveyor travel path relative to an opposing side of the travel path.

5. The system of claim 1, further comprising a control circuit that is configured to direct the wheel to rotate a defined distance then stop to receive a container from a container queue on the conveyor, and wherein the control circuit is configured to rotate the wheel when data from the at least one upper sensor confirms an upright container is in position in a receiving pocket of the wheel.

6. The system of claim 1, further comprising a control circuit that is configured to direct the conveyor to reverse direction when a fault condition is identified based on data from at least one of the at least one lower sensor.

7. The system of claim 1, further comprising a control circuit that is configured to direct the wheel to rotate with an empty receiving pocket to an indexed position when a fault condition associated with a fallen container is identified as located away from the receiving pocket based on data from the at least one lower sensor and the at least one upper sensor.

8. The system of claim 1, wherein the travel path narrows in width as it approaches the wheel, the system further comprising a curved sidewall that is concave proximate an outer perimeter of the wheel, wherein the at least one lower sensor comprises a retroreflective sensor that transmits a respective optical signal through a front edge portion of the receiving pocket.

9. The system of claim 2, wherein the second lower sensor is a retroreflective sensor, and wherein the second optical signal crosses the conveyor travel path a distance "D" away from the first optical signal, and wherein the distance D is greater than one diameter corresponding to between 1-2 inches but less than two diameters corresponding to between 2-4 inches of the elongated containers transported by the conveyor.

10. The system of claim 2, wherein the travel path narrows in width as it approaches the wheel to a width that is less than eight inches corresponding to a width that is less than four container diameters of containers having diameters between 1-2 inches, and wherein the system comprises a control circuit that is configured to identify a bridge of frictionally engaged upright containers based on data from at least the second lower sensor, then automatically reverse direction of the conveyor to dislodge the bridge.

11. The system of claim 1, further comprising a plurality of containers on the conveyor, wherein the containers are optically transmissive tubes with a top cap and holding biospecimens, wherein the first lower sensor is positioned to transmit the first optical signal at a height that is less than 1 inch so as to be no greater than an outer diameter of the containers.

12. The system of claim 11, wherein at least some of the containers comprise blood samples.

13. The system of claim 1, further comprising a control circuit that is configured to monitor the at least one upper sensor for a short interval after a fallen container fault is identified based on data from at least one of the at least one lower sensor to assess whether a container enters a receiving pocket of the wheel before generating a fallen container notification.

14. The system of claim 1, further comprising:
a pair of laterally spaced apart sidewalls facing each other across the conveyor, wherein the sidewalls have a parallel segment that merges into a curved segment where the sidewalls travel toward each other proximate the rotating wheel to have a width that is more narrow proximate the wheel than along the parallel segment, wherein the first lower sensor is held outside one sidewall of the curved segment; and
a bridge member that extends across and above the curved sidewalls held by the housing, wherein the at least one upper sensor is held by the bridge member.

15. The system of claim 2, wherein the first and second lower sensors comprise retroreflective sensors with a respective first and second reflector residing across the conveyor from and in optical communication with the corresponding first and second sensor such that the first reflector is oriented at a first angle and the second reflector is orientated at a second angle that is larger than the first angle, the first and second angles being between 10-60 degrees.

16. The system of claim 1, further comprising a control circuit that is configured to detect multiple different fault conditions associated with fallen containers adjacent or in the wheel and (i) direct the wheel to rotate a defined distance then stop to receive a container from a container queue on the conveyor, (ii) direct the wheel to rotate when data from the at least one upper sensor confirms an upright container is in position in a receiving pocket of the wheel, (iii) direct the conveyor to reverse direction when a fault condition is identified based on data from the at least one lower sensor, and (iv) direct the wheel to rotate with an empty receiving pocket to an indexed position when a fault condition associated with a fallen container is identified as located away from the receiving pocket based on data from the at least one lower sensor and the at least one upper sensor.

17. An automated detection apparatus for detection of microorganism growth in test samples, comprising:
a housing enclosing an interior temperature controlled chamber;
a container loading system comprising a conveyor defining a travel path that transports groups of elongated containers with test samples to the housing for processing;
a rotating wheel in cooperating alignment with the conveyor, the wheel having a plurality of circumferentially spaced apart pockets, each pocket configured to accept a single elongated container;
a detection device located within the housing configured to detect microorganism growth in specimen containers loaded into the housing; and
a plurality of spaced apart sensors residing proximate the wheel, the sensors including (i) at least one lower, sensor including a first lower sensor configured to transmit a respective optical signal across a portion of a pocket of the wheel at a loading position and (ii) at least one upper sensor that is positioned to transmit a respective upper optical signal at a height that is above the at least one lower sensor optical signal and corresponds to a top portion of an upright container to thereby allow detection of different orientations and positions of containers.

18. The apparatus of claim 17, wherein the at least one lower sensor comprises the first lower sensor and a second lower sensor with the first and second lower sensors positioned longitudinally spaced apart from each other, the first lower sensor being downstream of the second lower sensor, the first and second lower sensors configured to transmit respective first and second non-intersecting first and second optical signals across the conveyor container travel path proximate the rotating wheel, and wherein a height of each of the first and second optical signals is below a width dimension of 1-2 inches of the containers.

19. The apparatus of claim 17, further comprising a plurality of elongated containers on the conveyor, wherein the containers are optically transmissive tubes with a top cap and have a common size with an outer diameter, wherein the at least one lower sensor is positioned to transmit respective optical signals at a height that is no greater than 1-2 inches corresponding to a diameter of the containers.

20. The apparatus of claim 18, wherein the first and second optical signals diverge away from each other as they project across the conveyor so that the first and second optical signals are closer together on one side of the conveyor travel path relative to an opposing side of the travel path.

21. The apparatus of claim 17, wherein the apparatus comprises a control circuit that is configured to direct the wheel to rotate a defined distance then stop to receive a container from a container queue on the conveyor, and wherein the control circuit is configured to rotate the wheel when the upper sensor confirms an upright container is in position in a receiving pocket of the wheel.

22. The apparatus of claim 17, wherein the apparatus comprises a control circuit that is configured to direct the conveyor to reverse direction when a fault condition is identified based on data from at least one of the at least one upper and at least one lower sensors.

23. The apparatus of claim 17, wherein the apparatus comprises a control circuit that is configured to direct the wheel to rotate with an empty receiving pocket to an indexed position when a fault condition associated with a fallen container is identified as located away from the receiving pocket based on data from the at least one lower sensor.

24. The apparatus of claim 17, wherein the containers have a travel path that narrows in width as it approaches the wheel, the apparatus further comprising at least one curved upwardly extending sidewall that resides above a conveyor floor of the travel path that is concave proximate an outer perimeter of the wheel, and wherein the first lower sensor is a retroreflective sensor.

25. The apparatus of claim 18, wherein the first and second lower sensors are retroreflective sensors, and wherein the second lower sensor generates an optical signal that crosses the conveyor travel path a distance "D" away from the first lower sensor optical signal, wherein the distance D is greater than one diameter but less than two diameters of the elongated containers transported by the conveyor, and wherein D is in a range of about 1-2 inches.

26. The apparatus of claim 17, wherein the apparatus has a container travel path that narrows in width as it approaches the wheel to a width that is less than four container diameters, and wherein the apparatus comprises a control circuit that is configured to identify a bridge of frictionally engaged upright containers based on data from at least of the at least one lower sensor, then automatically reverse direction of the conveyor to dislodge the bridge.

27. The apparatus of claim 17, wherein the conveyor is substantially continuously moving during normal operation and the rotating wheel is indexed to rotate a defined distance, then stop for receiving a container in a loading position, and wherein the apparatus comprise a control circuit that controls the indexed rotation of the wheel and can stop and/or reverse a direction of the conveyor based on data from the at least one upper and lower sensors.

28. The apparatus of claim 17, further comprising a control circuit that is configured to monitor the at least one upper sensor for a short interval after a fallen container fault is identified based on data from the at least one lower sensor to assess whether a container enters a receiving pocket of the wheel before generating a fallen container notification.

29. The apparatus of claim 17, further comprising:
a pair of laterally spaced apart sidewalls facing each other across the conveyor, wherein the sidewalls have a parallel segment that merges into a curved segment where the sidewalls travel toward each other proximate the rotating wheel to have a width that is more narrow proximate the wheel than along the parallel segment, wherein the first lower sensor is held outside one sidewall of the curved segment; and
a bridge member that extends across and above the curved sidewalls held by the housing, wherein the at least one upper sensor is held by the bridge member.

30. The apparatus of claim 17, further comprising a control circuit that is configured to detect multiple different fault conditions associated with fallen containers adjacent or in the wheel and (i) direct the wheel to rotate a defined distance then stop to receive a container from a container queue on the conveyor, (ii) direct the wheel to rotate when data from the at least one upper sensor confirms an upright container is in position in a receiving pocket of the wheel, (iii) direct the conveyor to reverse direction when a fault condition is identified based on data from the at least one lower sensor, and (iv) direct the wheel to rotate with an empty receiving pocket to an indexed position when a fault condition associated with a fallen container is identified as located away from the receiving pocket based on data from the at least one lower sensor and the at least one upper sensor.

* * * * *